United States Patent [19]

Furutachi et al.

[11] 4,032,346

[45] June 28, 1977

[54] SILVER HALIDE EMULSION CONTAINING TWO-EQUIVALENT MAGENTA COUPLER

[75] Inventors: Nobuo Furutachi; Kotaro Nakamura; Minoru Yamada; Atsuaki Arai, all of Minami-ashigara, Japan

[73] Assignee: Fuji Photo Film Co., Ltd., Minami-ashigara, Japan

[22] Filed: July 31, 1975

[21] Appl. No.: 600,655

[30] Foreign Application Priority Data

Aug. 1, 1974 Japan .............................. 49-88417

[52] U.S. Cl. .................................... 96/56.5; 96/74; 96/100; 260/310 A
[51] Int. Cl.² ..................... G03C 7/00; G03C 1/40
[58] Field of Search ............... 96/100, 56.5, 56.6, 96/74; 260/310 A

[56] References Cited

UNITED STATES PATENTS

| | | | |
|---|---|---|---|
| 3,212,894 | 10/1965 | Menzel et al. | 96/56.6 |
| 3,576,636 | 4/1971 | Matsui et al. | 96/100 |

OTHER PUBLICATIONS

Papini et al., Chemical Abstracts, vol. 69, 59154f, (1968).

*Primary Examiner*—J. Travis Brown
*Attorney, Agent, or Firm*—Sughrue, Rothwell, Mion, Zinn & Macpeak

[57] ABSTRACT

A photographic two-equivalent magenta coupler, capable of forming a magenta color image upon coupling reaction with an oxidation product of an aromatic primary amine developing agent, represented by the following general formula I:

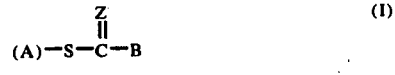

wherein (A) represents a residue of a magenta color image forming coupler;

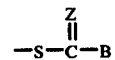

represents a group which is substituted for one hydrogen atom of the active methylene group in the coupler A; Z represents an oxygen atom or a sulfur atom; B represents a — Y group, a — D — Y group, or a

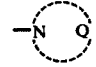

group; D represents an oxygen atom or an —NR — group; R represents a hydrogen atom, an alkyl group or an aryl group; Y represents an alkyl group, an aryl group or a heterocyclic group; and Q in the

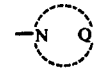

group represents the non-metallic atoms necessary to form a 5-membered or 6-membered nitrogen containing heterocyclic ring; and color photographic light-sensitive materials containing the two equivalent magenta coupler.

14 Claims, No Drawings

SILVER HALIDE EMULSION CONTAINING TWO-EQUIVALENT MAGENTA COUPLER

BACKGROUND OF THE INVENTION

1. Field of the Invention

The present invention relates to color photography and more particularly, it relates to a novel class of two-equivalent magenta couplers which are suitable for use in silver halide color photographic light-sensitive materials.

2. Description of the Prior Art

It is known that, by the color development of a silver halide color photographic material, a color developing agent of aromatic primary amine type is oxidized and is reacted with a coupler to form a dye, such as an indophenol, an indoaniline, an indamine, an azomethine, a phenoxazine, a phenazine and the like, thus forming a color image. In this type, the subtractive color process is ordinarily used for color reproduction and yellow, magenta and cyan color images are formed, which are respectively the complementary colors of blue, green and red. For example, a coupler of the acylacetanilide or dibenzoylmethane type is used for forming a yellow color image, a coupler of the pyrazolone, pyrazolobenzimidazole, cyanoacetophenone or indazolone type is used for forming a magenta color image and a coupler of the phenol type, such as a phenol and a naphthol, is used for forming a cyan color image.

In one of the most preferred embodiments of color photographic light-sensitive materials, the dye image forming couplers are incorporated into a silver halide emulsion. These couplers which are incorporated into the emulsion must be rendered nondiffusible (diffusion resistant) in the binder matrix of the emulsion.

The color image forming couplers of the prior art are almost all four-equivalent couplers which require theoretically four moles of silver halide as an oxidizing agent for forming one mole of the dye through the coupling reaction. On the contrary, a two-equivalent coupler having an active methylene group which is substituted with a group capable of being released through the coupling of an oxidized product of an aromatic primary amine developing agent requires only the development of two moles of silver halide for forming one mole of the dye. Since the quantity of silver halide required for forming a dye in the case of a two-equivalent coupler is one half of that required in the case of an ordinary four-equivalent coupler a two-equivalent coupler has many advantages because a thinner light-sensitive layer can be used and the layer can be processed rapidly. In addition, the photographic properties and economy can improved through a reduction in the layer thickness.

Several attempts have been made to convert 5-pyrazolone type couplers which have been conventionally used as a magenta color forming coupler to two-equivalent coupler by substituting a group capable of being split off for one of the hydrogen atoms at the 4-position of the 5-pyrazolone. For example, a pyrazolone in which the 4-position is substituted with a thiocyano group is described in U.S. Pat. Nos. 3,214,437 and 3,253,924, an acyloxy group is described in U.S. Pat. No. 3,311,476, an aryloxy group is described in U.S. Pat. No. 3,419,391, a 2-triazolyl group is described in U.S. Pat. No. 3,617,291, a halogen atom is described in U.S. Pat. No. 3,522,052, and the like.

However, when these 4-position substituted pyrazolone couplers are employed, some disadvantages occur, e.g., a remarkable color fog is produced, coupling reactivity is insufficient, the couplers per se are chemically unstable and change into compounds which can not form the dyes or many difficulties are encountered in the preparation thereof.

5-Pyrazolones in which the 4-position is substituted with as alkylthio group, an arylthio group or a heterocyclic thio group as described in U.S. Pat. No. 3,227,554 are also known. However, most of these known thio-substituted pyrazolone compounds have the disadvantages that their reactivity with the oxidation products of an aromatic primary amine color developing agent is not suitable, that the mercapto compounds which are formed upon the coupling reaction have such severe photographic effects that they cannot be used in a conventional color photographic light-sensitive material, and that the couplers are chemically unstable.

On the other hand, as couplers which can be used in a color developer solution, four-equivalent couplers have the disadvantage that a larger amount of silver halide is required to obtain a certain color image density, and previously known two-equivalent couplers do not provide preferred results since the couplers are not sufficiently stable in a color developer solution.

SUMMARY OF THE INVENTION

Therefore, an object of the present invention is to provide a novel two-equivalent magenta color image forming coupler in which the coupling position of the magenta coupler is substituted with a group capable of being released by the coupling reaction with an oxidation product of an aromatic primary amine developing agent.

Another object of the present invention is to provide a novel two-equivalent magenta coupler which has a suitable reactivity and which is capable of forming a dye with a high yield and without forming undesired stains and fog.

Another object of the present invention is to provide a color photographic light-sensitive material having a silver halide emulsion layer containing a novel magenta color image forming coupler.

Still another object of the present invention is to provide a method by which the amount of silver halide in the photographic emulsion layer is reduced and the sharpness of the color image obtained is improved by the use of a novel magenta color image forming coupler.

Still another object of the present invention is to provide a color photograph having a durable color image by the use of a novel magenta color image forming coupler.

A further object of the present invention is to provide a novel two-equivalent magenta coupler which can be prepared in a simple manner and in a high yield.

A further object of the present invention is to provide a novel two-equivalent magenta coupler which has an improved conversion rate to the dye, an excellent resistance to the effects of chemical compounds and a good coupling reactivity.

A still further object of the present invention is to provide a method of forming a dye image comprising developing an exposed silver halide photographic material with an aromatic primary amine developing agent in the presence of a novel two-equivalent magenta coupler in which the coupling position of the magenta color image forming coupler is substituted with a group capable of being released by the coupling reaction with an oxidation product of the aromatic primary amine developing agent.

A still further object of the present invention is to provide a method of forming a dye image by processing a silver halide photographic light-sensitive material with a color developer solution containing a novel two-equivalent magenta coupler in which the coupling position of the magenta color image forming coupler is substituted with a group capable of being released by the coupling reaction with an oxidation product of an aromatic primary amine developing agent.

These and other objects of the present invention will become apparent from the following detailed description and examples of the invention.

Accordingly, this invention provides a two-equivalent magenta coupler represented by the following general formula (I)

(I)

wherein (A) represents a residue of a magenta color image forming coupler;

represents a group which is substituted for one hydrogen atom of the active methylene group in the coupler, i.e., substituted in the coupling position; Z represents an oxygen atom or a sulfur atom; B represents a — Y group, a — D — Y group or an

group; D represents an oxygen atom or an — NR — group; R represents a hydrogen atom, an alkyl group or an aryl group; Y represents an alkyl group, an aryl group or a heterocyclic group; and Q in the

group represents the non-metallic atoms necessary to form a 5-membered or 6-membered nitrogen-containing heterocyclic group.

In another embodiment of this invention, this invention provides a silver halide color photographic light-sensitive material comprising a support having thereon at least one silver halide emulsion layer containing a two-equivalent magenta coupler, which is capable of forming a magenta color image upon coupling with an oxidation product of an aromatic primary amine developing agent, represented by the general formula (I).

This invention in another embodiment provides a method of forming color images which comprises processing an exposed silver halide color photographic light-sensitive material comprising a support having thereon at least one silver halide emulsion layer with a color developer containing an aromatic primary amine developing agent in the presence of the two-equivalent magenta coupler represented by the general formula (I) described above.

In a further embodiment, this invention provides a method of forming color images comprising developing an exposed silver halide photographic light-sensitive material with a color developer solution containing the two-equivalent magenta coupler represented by the general formula (I).

DETAILED DESCRIPTION OF THE INVENTION

In the above formula, (A) can represent any residue of a magenta color image forming coupler, and represents preferably a 5-oxo-4-pyrazolinyl group or a 3-pyrazolo-[1,5-a]-benzimidazolyl group.

Useful couplers for the present invention are represented by the general formulae II, III, IV, V, VI and VII.

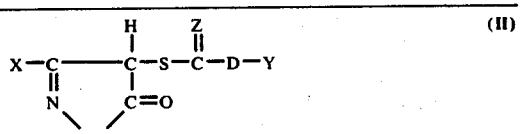

(II)

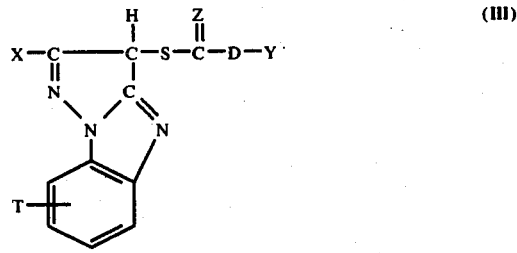

(III)

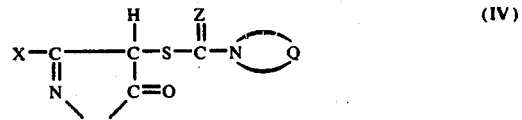

(IV)

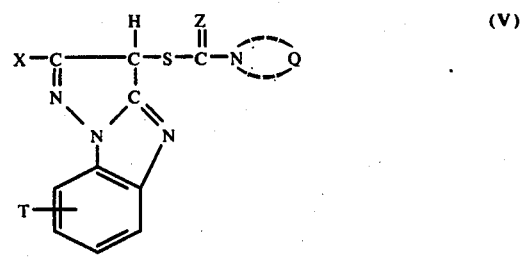

(V)

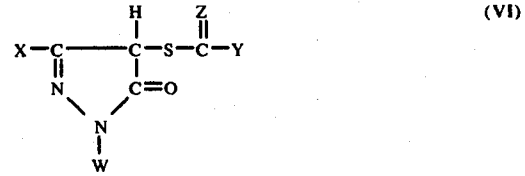

(VI)

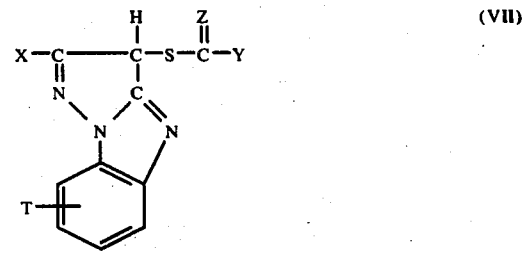

(VII)

wherein W represents a hydrogen atom or a group having up to 40 carbon atoms, preferably up to 22 carbon atoms. Suitable groups for W include a straight chain or branched chain alkyl group (for example, a methyl, ethyl, isopropyl, tert-butyl, hexyl, dodecyl, etc. group); an alkenyl group (for example, an allyl, β-vinylethyl, etc. group); a cycloalkyl group (for example, a cyclopentyl, cyclohexyl, norbornyl, 7,7-dialkylnorbornyl, 2-pentadecyl-7,7-dialkylnorbornyl, etc. group); an aralkyl group (for example, a benzyl, β-phenylethyl, etc. group); a cycloalkenyl group (for example, a cyclopentenyl, cyclohexenyl, etc. group). These groups can be substituted with a substituent selected from a halogen atom (e.g., chlorine, bromine, fluorine, etc.), and a nitro, cyano, aryl (e.g., phenyl, tolyl, methoxyphenyl, naphthyl, etc.), alkoxy (e.g., methoxy, butoxy, octyloxy, etc.), aryloxy (e.g., phenoxy, tolyloxy, naphthoxy, etc.), carboxy, alkylcarbonyl (e.g., methylcarbonyl, propylcarbonyl, etc.), arylcarbonyl (e.g., phenylcarbonyl, etc.), alkoxycarbonyl (e.g., methoxycarbonyl, butoxycarbonyl, etc.), aryloxycarbonyl (e.g., phenoxycarbonyl, tolyloxycarbonyl, etc.), sulfo, acyloxy (e.g., acetoxy, propionyloxy, hexanoyloxy, etc.), sulfamoyl (e.g., N-methylsulfamoyl, N,N-diethylsulfamoyl, N-methyl-N-phenylsulfamoyl, etc.), carbamoyl (e.g., N-ethylcarbamoyl, N-methyl-N-decylcarbamoyl, phenylcarbamoyl, etc.), acylamino (e.g., acetamido, butyramido, benzamido, etc.), diacylamino (e.g., phthalimido, etc.), ureido (e.g., ethylureido, phenylureido, chlorophenylureido, etc.), thioureido (e.g., ethylthioureido, phenylthioureido, etc.), alkoxycarbonylamino (e.g., a methoxycarbonylamino, octoxycarbonylamino, etc.), aryloxycarbonylamino (e.g., phenoxycarbonylamino, tolyloxycarbonylamino, etc.) alkoxythiocarbonylamino (e.g., methoxythiocarbonylamino, octoxythiocarbonylamino, etc.), aryloxythiocarbonylamino (e.g., phenoxythiocarbonylamino, tolyloxythiocarbonylamino, etc.), sulfonamido (e.g., methylsulfonamido, ethylsulfonamido, phenylsulfonamido, etc.), heterocyclic (e.g., 1-imidazolyl, 2-imidazolyl, 2-benzothiazolyl, 2-oxazolyl, 2-thienyl, 2-pyridyl, 4-pyridyl, 2-benzofuryl, 2-benzimidazolyl, etc.), arylsulfonyloxy (e.g., phenylsulfonyloxy, tolylsulfonyloxy, etc.), alkylsulfonyloxy (e.g., methylsulfonyloxy, etc.), arylsulfonyl (e.g., phenylsulfonyl, etc.), alkylsulfonyl (e.g., propylsulfonyl, ethylsulfonyl, etc.), arylthio (e.g., phenylthio, tolylthio, etc.), alkylthio (e.g., methylthio, octylthio, dodecylthio, etc.), alkylsulfinyl (e.g., methylsulfinyl, etc.), arylsulfinyl (e.g., phenylsulfinyl, etc.), alkylamino (e.g., methylamino, butylamino, etc.), dialkylamino (e.g., N,N-dimethylamino, N-methyl-N-octylamino, etc.), anilino, N-arylanilino (e.g., N-phenylanilino, etc.), N-alkylanilino (e.g., N-methylanilino, etc.), heterocyclic amino (e.g., 2-oxazolylamino, 2-thiazolylamino, etc.), N-alkyl-N-heterocyclic amino (e.g., an N-methyl-N-(2-oxazolyl)amino, N-ethyl-N-(2-pyridyl)amino, etc.), N-aryl-N-heterocyclic amino (e.g., N-phenyl-N-(2-pyridyl)amino, etc.), N-acylamino-N-heterocyclic amino (e.g., N-acetyl-N-(2-benzimidazolyl)amino, etc.), N-acylanilino (e.g., N-acetylanilino, etc.), hydroxy and mercapto group.

Further, W represents an aryl group (for example, a phenyl, α- or β-naphthyl, etc. group); and an aryl group having one or more substituents. Such aryl group substituents can be selected from a halogen atom (e.g., chlorine, bromine, fluorine, etc.) and alkyl (e.g., methyl, ethyl, octyl, etc.), alkenyl (e.g., allyl, β-vinylethyl, etc.), cycloalkyl (e.g., cyclopentyl, cyclohexyl, etc.), aralkyl (e.g., benzyl, β-phenethyl, etc.), cycloalkenyl (e.g., cyclopentenyl, cyclohexenyl, etc.), nitro, cyano, aryl (e.g., phenyl, naphthyl, etc.), alkoxy (e.g., methoxy, butoxy, octyloxy, etc.), aryloxy (e.g., phenoxy, tolyloxy, naphthoxy, etc.), carboxy, alkylcarbonyl (e.g., methylcarbonyl, propylcarbonyl, etc.), arylcarbonyl (e.g., phenylcarbonyl, etc.), alkoxycarbonyl (e.g., methoxycarbonyl, butoxycarbonyl, etc.), aryloxycarbonyl (e.g., phenoxycarbonyl, etc.), sulfo, acyloxy (e.g., acetoxy, propionyloxy, hexanoyloxy, etc.), sulfamoyl (e.g., phenylsulfamoyl, methylsulfamoyl, etc.), carbamoyl such as alkylcarbamoyl, dialkylcarbamoyl, arylcarbamoyl, etc., (e.g., N-ethylcarbamoyl, N-methyl-N-decylcarbamoyl, phenylcarbamoyl, etc.), acylamino (e.g., acetamido, butyramido, benzamido, etc.), diacylamino (e.g., phthalimido, etc.), ureido (e.g., methylureido, phenylureido, etc.), thioureido (e.g., propylthioureido, phenylthioureido, etc.), alkoxycarbonylamino (e.g., methoxycarbonylamino, octoxycarbonylamino, etc.), aryloxycarbonylamino (e.g., phenoxycarbonylamino, tolyloxycarbonylamino, etc.), alkoxythiocarbonylamino (e.g., methoxythiocarbonylamino, octoxythiocarbonylamino, etc.), aryloxythiocarbonylamino (e.g., phenoxythiocarbonylamino, tolyloxythiocarbonylamino, etc.), sulfonamido (e.g., methylsulfonamido, phenylsulfonamido, etc.), heterocyclic (e.g., 1-imidazolyl, 2-imidazolyl, 2-benzothiazolyl, 2-oxazolyl, 2-thienyl, 2-pyridyl, 4-pyridyl, 2-benzofuryl, 2-benzimidazolyl, etc.), arylsulfonyloxy (e.g., phenylsulfonyloxy, tolylsulfonyloxy, etc.), alkylsulfonyloxy (e.g., methylsulfonyloxy, etc.), arylsulfonyl (e.g., phenylsulfonyl, etc.), alkylsulfonyl (e.g., propylsulfonyl, ethylsulfonyl, etc.), arylthio (e.g., phenylthio, tolylthio, etc.), alkylthio (e.g., methylthio, octylthio, dodecylthio, etc.), alkylsulfinyl (e.g., methylsulfinyl, etc.), arylsulfinyl (e.g., phenylsulfinyl, etc.), alkylamino (e.g., methylamino, butylamino, etc.), dialkylamino (e.g., N,N-dimethylamino, N-methyl-N-octylamino, etc.), anilino, N-alkylanilino (e.g., N-methylanilino, etc.), N-arylanilino (e.g., N-phenylanilino, etc.), N-acylanilino (e.g., N-acetylanilino, etc.), hydroxy and mercapto group.

A phenyl group in which at least one of the orthopositions is substituted with an alkyl group, an alkoxy group or a halogen atom is particularly useful for W, since when the coupler remains in a color photographic material after development, less print-out by the action of light or heat occurs.

Furthermore, W represents a heterocyclic group (for example, a 5-membered or 6-membered heterocyclic group or a condensed heterocyclic group containing one or more of a nitrogen atom, an oxygen atom or a sulfur atom, as a hetero atom, such as a pyridyl, quinolyl, furyl, benzothiazolyl, oxazolyl, imidazolyl, naphthoxazolyl, etc. group); or a substituted heterocyclic group containing one or more of the substituents described above for the aryl group.

Furthermore, W represents an acyl group (e.g., a tetradecanoyl, etc. group, a toluenesulfonyl, etc. group), a thioacyl group (e.g., a tridecylthiocarbonyl, etc. group), an alkylsulfonyl group (e.g., a methylsulfonyl, octylsulfonyl, etc. group), an arylsulfonyl group (e.g., a phenylsulfonyl, tolylsulfonyl, etc. group), an alkylsulfinyl group (e.g., a methylsulfinyl, etc. group), an arylsulfinyl group (e.g., a phenylsulfinyl, etc. group), a carbamoyl group (e.g., a tetradecylcarbamoyl, etc. group), and a thiocarbamoyl group (e.g., an N,N-diethylthiocarbamoyl, etc. group).

X represents a hydrogen atom or a group having up to 40 carbon atoms, preferably up to 22 carbon atoms. Suitable groups for X include a straight chain or branched chain alkyl group, an alkenyl group, a cycloalkyl group, an aralkyl group and a cycloalkenyl group, e.g., as previously defined for W. These groups can contain one or more of the substituents described above for W.

Further, X repesents an aryl group, e.g., as defined for W, or a heterocyclic group, e.g., as defined for W, and these groups can contain one or more of the substituents described above for W.

Furthermore, X represents an alkoxycarbonyl group (for example, a methoxycarbonyl, ethoxycarbonyl, stearyloxycarbonyl, etc. group); an aryloxycarbonyl group (for example, a phenoxycarbonyl, α- or β-naphthoxycarbonyl, etc. group); an aralkyloxycarbonyl group (for example, a benzyloxycarbonyl, etc. group); an alkoxy group (for example, a methoxy, ethoxy, dodecyloxy, etc. group); an aryloxy group (for example, a phenoxy, tolyloxy, etc. group); an alkylthio group (for example, an ethylthio, dodecylthio, etc. group); an arylthio group (for example, a phenylthio, α-naphthylthio, etc. group); a carboxy group; an acylamino group (for example, an acetamido, 3-[(2,4-di-tertamylphenoxy)acetamido]benzamido, etc. group); a diacylamino group (e.g., a phthalimido, etc. group); an N-alkylacylamino group (for example, an N-methylpropionamido, etc. group); an N-arylacylamino group (for example, an N-phenylacetamido, etc. group); a ureido group (for example, a ureido, N-arylureido (e.g., phenylureido, etc.), N-alkylureido (e.g., ethylureido, etc.), etc. group); a thioureido group (for example, a thioureido, N-arylthioureido (e.g., phenylthioureido, etc.), N-alkylthioureido (e.g., ethylthioureido, etc.), etc. group); an alkoxycarbonylamino group (e.g., a methoxycarbonylamino, octoxycarbonylamino, etc. group), an aryloxycarbonylamino group (e.g., a phenoxycarbonylamino, tolyloxycarbonylamino, etc. group), an alkoxythiocarbonylamino group (e.g., a methoxythiocarbonylamino, octoxythiocarbonylamino, etc. group), an aryloxythiocarbonylamino group (e.g., a phenoxythiocarbonylamino, tolyloxythiocarbonylamino, etc. group); an anilino group (for example, an anilino (e.g., phenylamino, 2-chloro-5-tetradecanamidoanilino, etc.), N-alkylanilino (e.g., N-methylanilino, etc.), N-arylanilino (e.g., N-phenylanilino, etc.), N-acylanilino (e.g., N-acetyl-(2-chloro-5-tetradecyloxycarbonyl)anilino, etc.), etc. group); an alkylamino group (for example, an N-alkylamino (e.g., an n-butylamino, etc.), N,N-dialkylamino (e.g., N,N-di-n-butylamino, etc.), cycloalkylamino (e.g., cyclohexylamino, etc.), etc. group); a cycloamino group (for example, a piperidino, pyrrolidino, etc. group); an alkylcarbonyl group (for example, a methylcarbonyl, etc. group); an arylcarbonyl group (for example, a phenylcarbonyl, etc. group); a sulfonamido group (for example, an alkylsulfonamido (e.g., methanesulfonamido, etc.), arylsulfonamido (e.g., benzenesulfonamido, etc.), etc. group); a carbamoyl group (for example, an N-alkylcarbamoyl (e.g., tetradecylcarbamoyl, etc.), N,N-dialkylcarbamoyl (e.g., N-methyl-N-octadecylcarbamoyl, etc.), N-alkyl-N-arylcarbamoyl (e.g., N-methyl-N-phenylcarbamoyl, etc.), N-arylcarbamoyl (e.g., phenylcarbamoyl, etc.), N,N-diarylcarbamoyl (e.g., N,N-diphenylcarbamoyl, etc.), etc. group); a sulfamoyl group (for example, an N - alkylsulfamoyl (e.g., α-(2,4-di-tertamylphenoxy)propylsulfamoyl, etc.), N,N-dialkylsulfamoyl (e.g., N-methyl-N-octadecylsulfamoyl, etc.), N-arylsulfamoyl (e.g., phenylsulfamoyl, etc.), N-alkyl-N-arylsulfamoyl (e.g., N-methyl-N-phenylsulfamoyl, etc.), N,N-diarylsulfamoyl (e.g., N,N-diphenylsulfamoyl, etc.), etc. group); a guanidino group (for example, an N-alkyl guanidino (e.g., N-methylguanidino, etc.), N-arylguanidino (e.g., N-phenylguanidino, etc.), etc. group); a cyano group; an acyloxy group (for example, a tetradecanoyloxy, etc. group); a sulfonyloxy group (for example, an alkylsulfonyloxy (e.g., methylsulfonyloxy, etc.), arylsulfonyloxy (e.g., benzenesulfonyloxy, etc.), etc. group); a hydroxy group; a mercapto group; a halogen atom (e.g., a chlorine, bromine, fluorine, or iodine atom); or a sulfo group.

T represents a hydrogen atom or a group having up to 40 carbon atoms, preferably up to 22 carbon atoms. Suitable groups for T include a straight chain or branched chain alkyl group, an alkenyl group, a cycloalkyl group, an aralkyl group and a cycloalkenyl group, e.g., as described above for W. These groups can contain one or more of the substituents described above for W.

Further, T represents an aryl group or a heterocyclic group, e.g., as described above for W and these groups can contain one or more of the substituents described above for W.

Furthermore, T represents a halogen atom, and a cyano, alkoxy, aryloxy, carboxy, alkoxycarbonyl, aryloxycarbonyl, acyloxy, alkylcarbonyl, arylcarbonyl, alkylthiocarbonyl, arylthiocarbonyl, sulfo, sulfamoyl, carbamoyl, acylamino, diacylamino, ureido, thioureido, alkoxycarbonylamino, aryloxycarbonylamino, alkoxythiocarbonylamino, aryloxythiocarbonylamino, sulfonamido, alkylsulfonyloxy, arylsulfonyloxy, arylsulfonyl, alkylsulfonyl, arylthio, alkylthio, alkylsulfinyl, arylsulfinyl, alkylamino, dialkylamino, anilino, N-arylamino, N-alkylanilino, N-acylanilino, hydroxy or mercapto group, e.g., as described for W above.

Y has up to 40 carbon atoms and represents an alkyl group, an aryl group or a heterocyclic group.

Suitable alkyl groups for Y include a straight chain or branched chain alkyl group (for example a methyl, ethyl, isopropyl, butyl, isobutyl, dodecyl, stearyl, etc., group); an alkenyl group (for example, an allyl, oleyl, etc., group); a cycloalkyl group (for example, a cyclopentyl, cyclohexyl, etc., group); an aralkyl group (for example, a benzyl, β-naphthylethyl, etc., group); or a cycloalkenyl group (for example, a cyclopentenyl, cyclohexenyl, etc., group). These groups can be substituted with one or more of a halogen atom, a nitro, cyano, aryl, alkoxy, aryloxy, carboxy, alkylcarbonyl, arylcarbonyl, alkoxycarbonyl, aryloxycarbonyl, sulfo, sulfamoyl, carbamoyl, acylamino, diacylamino, ureido, thioureido, alkoxycarbonylamino, aryloxycarbonylamino, alkoxythiocarbonylamino; aryloxythiocarbonylamino, heterocyclic, arylsulfonyl, alkylsulfonyl, arylsulfonyloxy, alkylsulfonyloxy, arylthio, alkylthio, alkylsulfinyl, arylsulfinyl, substituted amino group (for example, an N,N-dialkylamino, anilino, N-acylanilino, N-arylanilino, etc., group), or the like as described above for W.

Suitable aryl groups for Y include a mono or polycyclic aryl group (such as a phenyl, α-naphthyl, β-naphthyl, substituted phenyl, substituted α-naphthyl, substituted β-naphthyl, etc., group). These groups can be substituted with one or more of a halogen atom or an alkyl, aralkyl, alkenyl, cycloalkyl, cycloalkenyl, nitro, cyano, aryl, alkoxy, aryloxy, carboxy, alkylcarbonyl, arylcarbonyl, alkoxycarbonyl, aryloxycarbonyl, sulfo, acyloxy, sulfamoyl, N,N-dialkylsulfamoyl, N-alkyl-N-arylsulfamoyl, N-alkylsulfamoyl, N-arylsulfamoyl, carbamoyl, N-alkylcarbamoyl, N,N-dialkylcarbamoyl, N-alkyl-N-arylcarbamoyl, N-arylcarbamoyl, acylamino, diacylamino, ureido, thioureido, sulfonamido, alkoxycarbonylamino, aryloxycarbonylamino, alkoxythiocarbonylamino, aryloxythiocarbonylamino, heterocyclic, alkylsulfonyl, arylsulfonyl, alkylthio, arylthio, alkylsulfinyl, arylsulfinyl, or substituted amino group (for example an N,N-dialkylamino, anilino, N-acylanilino, N-arylanilino, etc.) group, and the like, as described above for W.

Suitable examples of heterocyclic groups for Y include a nitrogen-containing heterocyclic group (for example, a pyridyl, quinolyl, pyrrolidyl group, etc.), a heterocyclic group containing two or more nitrogen atoms (such as a benzimidazolyl group, etc. and these groups can be substituted with one or more of the substituents described above for the aryl group of Y; a oxygen containing heterocyclic group (for example, a tetrahydrofurfuryl, benzofuryl, etc., group) and these groups can be substituted with one or more of the substituents described above for the aryl group of Y; a sulfur-containing heterocyclic group (for example, a thienyl, benzothienyl, etc., group and these groups can be substituted with one or more of the substituents described above for the aryl group of Y; and a heterocyclic group containing two or more kinds of hetero atoms (for example, a benzoxazolyl, benzothiazolyl, etc. group).

Z represents an oxygen and a sulfur atom.

For Y the above described alkyl and aryl groups are preferred.

D represents an oxygen atom or an —NR— group, linking the Y group and the

group, and R represents an alkyl or aryl group, e.g., as described above for Y or a hydrogen atom.

Q in the

group represents the non-metallic atoms necessary to form a 5-membered or 6-membered nitrogen containing heterocyclic group. Preferred heterocyclic rings include pyrrolidine, piperidine, morpholine, imidazole, benzimidazole, phthalimide, succinimide, glutarimide, hydantoin, oxazolidinedione, benzetriazole, α-pyridone, β-pyridone, oxazolidone, valerolactam, butyrolactam, thiohydantoin, naphthotriazole, tetrazole, pyrazole, indole, imidazoline, pyrazoline, piperazine, indoline, isoindoline, and the like.

The coupler represented by the general formulae II, III, IV, V, VI and VII of the present invention can combine directly at W, X, Y or T or through a divalent group derived from W, X, Y or T to form asymmetrical or a symmetrical complex coupler.

The magenta coupler used in the present invention can provide various properties depending on the W, X, Y

and T substituents and this feature is suitable for achieving various photographic objects. When at least one of W, X, Y, T and

contains a hydrophobic group of 8 or more carbon atoms, the coupler associates in a hydrophilic colloid and becomes nondiffusible in the hydrophilic colloid layer of a light-sensitive material. Such a coupler can be incorporated in a silver halide emulsion layer. When Y or

contains a diffusion resistant hydrophobic group and at least one of W, X and T contains a watersolubilizing group such as a sulfo group or a carboxy group, the coupler per se is non-diffusible but provides a diffusible dye on the oxidizing coupling reaction with an aromatic primary amine developing agent. Such a diffusible dye providing coupler is suitable for use in diffusion transfer color photography.

The process of forming a dye image by the oxidizing coupling reaction with an aromatic primary amine developing agent can be divided mainly into two types depending on the method of adding a coupler. In one type, the so-called "coupler-in-the-emulsion type", the coupler is incorporated in an emulsion during the production of the light-sensitive material. In the other type, the so-called "coupler-in-the-developer type", the coupler is dissolved in a developer solution and diffused into the emulsion layer during development.

The "coupler" used-in-the coupler in emulsion "type" must be fixed in the emulsion layer, that is, must be diffusion-resistant. If the coupler is not diffusion-resistant, the coupler migrates in the light-sensitive material and the dye is formed in the wrong light-sensitive emulsion layer, thus markedly deteriorating the color reproduction capability of the light-sensitive material.

In order to render a coupler diffusion-resistant, a group containing a hydrophobic residue of 8 to 32 carbon atoms is introduced into the coupler molecule. This residue is generally called a "ballast group". The ballast group can be bonded to the coupler skeleton directly or through an imino bond, an ether bond, a carbonamido bond, a sulfonamido bond, an ureido bond, an ester bond, an imido bond, a carbamoyl bond, a sulfamoyl bond, and the like.

Some examples of ballast groups are shown in the specific examples of the coupler according to the present invention set forth hereinafter.

Specific examples of suitable ballast groups are as follows.

I. Alkyl groups and alkenyl groups For example, —CH$_2$—CH(C$_2$H$_5$)$_2$, —C$_{12}$H$_{25}$, —C$_{16}$H$_{33}$, —C$_{17}$H$_{33}$ II. Alkoxyalkyl groups For example, —(CH$_2$)$_3$—O—(CH$_2$)$_7$CH$_3$, $-(CH_2)_3OCH_2-CH-(CH_2)_nCH_3$
                  |
                  $C_2H_5$ as described in Japanese Patent Publication No. 27563/1964.

III. Alkylaryl groups
For example,

[structure: phenyl-$C_9H_{19}$]

[structure: phenyl with $C_4H_9(t)$ and $C_4H_9(t)$ substituents]

IV. Alkylaryloxyalkyl group
For example,

[structure: $-CH_2O-$phenyl with $C_5H_{11}(t)$ and $C_5H_{11}(t)$]

[structure: $-CH_2O-$phenyl with $C_5H_{11}(t)$ and $C_5H_{11}(sec)$]

[structure: $-CH(C_2H_5)O-$phenyl with $C_5H_{11}(t)$ and $C_5H_{11}(t)$]

[structure: $-(CH_2)_3-O-$phenyl with $C_5H_{11}(t)$ and $C_5H_{11}(t)$]

[structure: $-CH(C_2H_5)O-$phenyl with $C_{15}H_{31}(n)$]

[structure: $-CH_2O-$phenyl with $C_5H_{11}(t)$ and $CH_3-C(CH_3)(CH_2C_4H_9(t))-$]

[structure: $-CH(C_2H_5)O-$phenyl with Cl, $C_5H_{11}(t)$ and $C_5H_{11}(t)$]

V. Acylamidoalkyl groups
For example, $-CH_2CH_2N\begin{smallmatrix}COC_{15}H_{31}\\C_4H_9\end{smallmatrix}$ $-CH_2CH_2N\begin{smallmatrix}COC_{13}H_{27}\\C_3H_7\end{smallmatrix}$ $-CH_2CH_2NHCOCH_2CH_2N\begin{smallmatrix}COC_{13}H_{27}\\C_3H_7\end{smallmatrix}$ as described in U.S. Pat. Nos. 3,337,344 and 3,418,129.

VI. Alkoxyaryl groups and aryloxyaryl groups
For example,

[structure: phenyl-$OC_{18}H_{37}(n)$]

[structure: phenyl-O-phenyl-$C_{12}H_{25}(n)$]

VII. Residues containing both a long chain aliphatic group such as an alkyl group or an alkenyl group and a water-solubilizing group such as a carboxy group or a sulfo group
For example, $-CH-CH=CH-C_{16}H_{33}$
  |
  $CH_2COOH$ $-CH-C_{16}H_{33}$
  |
  $SO_3H$ VIII. Alkyl groups substituted with an ester group
For example, $-CH-C_{16}H_{33}(n)$
  |
  $COOC_2H_5$ $-CH_2CH_2-COOC_{12}H_{25}(n)$ IX. Alkyl groups substituted with an aryl group or a heterocyclic group
For example,

[structure: $-CH_2CH_2-$phenyl$-NHCOCH(COOCH_3)-C_{18}H_{37}(n)$]

[structure: $-CH_2CH_2-$phenyl-N(succinimide with $C_{16}H_{37}(n)$)]

X. Aryl groups substituted with an aryloxyalkoxycarbonyl group

For Example,

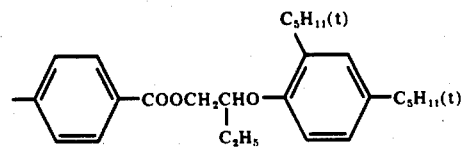

A coupler dispersion of the coupler of the present invention can be advantageously prepared by dissolving the coupler into either an organic solvent which has a high boiling point higher than about 170° C and is immiscible with water, a low boiling organic solvent and a water soluble organic solvent or a high boiling water-immiscible organic solvent and/or a low boiling organic solvent and/or a water soluble organic solvent.

High boiling water-immiscible organic solvents described in U.S. Pat. No. 2,322,027 can be used as the solvent. Examples of preferred solvents are di-n-butyl phthalate, benzyl phthalate, triphenyl phosphate, tri-o-cresyl phosphate, diphenyl mono-o-chlorophenyl phosphate, monophenyl di-o-chlorophenyl phosphate, dioctyl phthalate, dibutyl sebacate, acetyltributyl citrate, tri-tert-octyl trimelitate, n-nonyl-phenol, dioctyl butyl phosphate, N,N-diethyl laurylamide, 3-pentadecylphenyl ethyl ether, 2,5-di-sec-amylphenyl butyl ether, and the like.

Low boiling (lower than about 170° C) or water-soluble organic solvents which can be used together with or in place of the high boiling solvent are described in U.S. Pat. Nos. 2,801,171; 2,801,170; 2,949,360; etc. Examples of these organic solvents are as follows:

1. Organic solvents which have a low boiling point and are substantially insoluble in water such as methyl acetate, ethyl acetate, propyl acetate, butyl acetate, isopropyl acetate, ethyl propionate, secondary-butyl alcohol, ethyl formate, butyl formate, nitromethane, nitroethane, carbon tetrachloride, chloroform, and the like.

2. Water-soluble organic solvents such as methyl isobutyl ketone, β-ethoxyethylacetate, Carbitol acetate (diethyleneglycol monoacetate), methoxytriglycol acetate, acetyl acetone, diacetonealcohol, butyl Carbitol, methyl Carbitol, methyl ethyl ketone, methanol, ethanol, acetonitrile, dimethylformamide, dioxane, and the like. Preferably, the solvent has a sufficiently low water content so that the solubility of coupler is not adversely affected.

A method for removing the low boiling or water soluble solvent from a coupler dispersion which comprises air-drying the cooled noodle-like dispersion or washing the cooled noodle-like dispersion continuously with water described in U.S. Pat. No. 2,801,171 can be employed.

For the dispersion of an oil-soluble coupler, an emulsifying homogenizer, a colloid mill, an ultrasonic wave emulsifying apparatus, and the like are suitable. A diffusion resistant coupler having both a ballast group and a carboxylic acid group or a sulfonic acid group in the molecule is soluble in a neutral or weakly alkaline aqueous solution. The coupler can be incorporated in a photographic emulsion by adding such an aqueous solution containing the coupler to the photographic emulsion. The coupler is believed to be diffusion resistant through the formation of micelles in the hydrophilic polymer.

Specific examples of couplers according to the present invention are set forth below, but the present invention is not to be construed as being limited to only these couplers.

Coupler (1)

[1-(2,4,6-Trichlorophenyl)-3-{2-chloro-4-[α-(2,4-ditert-amylphenoxy)butyramido]anilino}-5-oxo-2-pyrazolin-4-yl]-N,N-dimethylaminecarbodithioate Coupler (2)

[1-(2,4,6-Trichlorophenyl)-3-{[3-(2,4-di-tert-amylphenoxy)acetamido]benzamido}-5-oxo-2-pyrazolin-4-yl]-octylaminecarbodithioate Coupler (3)

{1-(2,4,6-Trichlorophenyl)-3-[2-chloro-5-(tetradecanamido)anilino]-5-oxo-2-pyrazolin-4-yl}-N,N-diethylaminecarbodithioate Coupler (4)

[1-(2,4,6-Trichlorophenyl)-3-{3-[α-(2,4-di-tert-amylphenoxy)butyramido]benzamido}-5-oxo-2-pyrazolin-4-yl]-1-pyrrolidinecarbodithioate Coupler (5)

S-[1-(2,4,6-Trichlorophenyl)-3-{2-chloro-5-[γ-(2,4-di-tert-amylphenoxy)propylsulfamoyl]anilino}-5-oxo-2-pyrazolin-4-yl]thiobenzoate Coupler (6)

S-[1-(2,4,6-Trichlorophenyl)-3-(3,5-dicarboxyanilino)-5-oxo-2-pyrazolin-4-yl]-(3-tetradecanamidophenyl)-dithiocarbonate Coupler (7)

S-{1-[α-(2,4-Di-tert-amylphenoxy)butyramido]phenyl-3-methyl-5-oxo-2-pyrazolin-4-yl}ethyldithiocarbonate Coupler (8)

[1-(2,6-Dichloro-4-methoxyphenyl)-3-{3-[α-(3-tert-butyl-4-hydroxyphenoxy)tetradecanamido]benzamido}-5-oxo-2-pyrazolin-4-yl]-N-ethyl-N-propylaminecarbodithioate Coupler (9)

[1-(2,6-Dichloro-4-methoxyphenyl)-3-{3-[α-2,4-di-tertamylphenoxy)butyramido]benzamido}-5-oxo-2-yl]dodecanecarbodithioate Coupler (10)

[1-(2,6-Dichloro-4-methoxyphenyl)-3- 3-[α-(2,4-di-tertamylphenoxy)butyramido]benzamido -5-oxo-2-pyrazolin-4-yl]-1-naphthalenecarbodithioate Coupler (11)

(1-phenyl-3-methyl-5-oxo-2-pyrazolin-4-yl)-1-morpholinecarbodithioate

Coupler (12)

[1{2,6-Dichloro-4-[α-(3-pentadecylphenoxy)butyramido]-phenyl}-3-(2,4-dichloroanilino)-5-oxo-2-pyrazolin-4-yl]-1-imidazolecarbodithioate

Coupler (13)

[1-(2,6-Dichloro-4-sulfophenyl)-3-(2,4-dichloroanilino)-5-oxo-2-pyrazolin-4-yl)-octylaminecarbodithioate

Coupler (14)

S-[1-(2,4,6-Trichlorophenyl)-3-{3-[α-(2,4-di-tert-amylphenoxy)butyramido]phenylureido}-5-oxo-2-pyrazolin-4-yl]-thiopropionate

Coupler (15)

{1-(2,4,6-Trichlorophenyl)-3-[2-chloro-5-(β-carboxypentadecanamido)anilino]-5-oxo-2-pyrazolin-4-yl}-N-ethyl-N-phenylaminecarbodithioate

Coupler (16)

[1-(2,4,6-Trichlorophenyl)-3-(2-chloro-5-hexadecyloxycarbonylanilino)-5-oxo-2-pyrazolin-4-yl]-1-benzotriazolecarbodithioate

Coupler (17)

S-(1-(2,4,6-Trichlorophenyl)-3-(2-chloro-5-tetradecanamidoanilino)-5-oxo-2-pyrazolin-4-yl]-2-pyridinecarbodithioate

Coupler (18)

{(2-n-Heptadecyl-3H-pyrazolo-[1,5-a]-benzimidazol-3-yl}-N,N-diethylaminecarbodithioate

Coupler (19)

[2- 3-[α-(2,4-Di-tert-amylphenoxy)butyramido]-benzamido -3H-pyrazolo-[1,5-a]-benzimidazol-3-yl]-morpholinecarbodithioate

Coupler (20)

[2-{3-[α-(2,4-Di-tert-amylphenoxy)butyramido]-}5-oxo-2-pyrazolin-4-yl]-dodecanaminecarbodithioate

Coupler (21)

[1-(2,6-Dichloro-4-methoxyphenyl)-3-(3-acetamidobenzamido)-5-oxo-2-pyrazolin-4-yl]-{3-[α-(3-tert-butyl-4-hydroxyphenoxy)tetradecanamido]-phenoxy}carbodithioate The coupler of the present invention can be prepared, in general, by reacting a four-equivalent coupler and a disulfide according to the following reaction schematic:

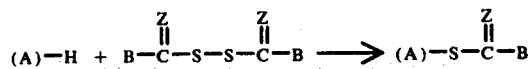

wherein (A), B and Z each has the same meaning as defined previously, and the hydrogen atom of (A)-H is connected to the coupling position of the residue of magenta color image forming coupler.

The reaction between the four-equivalent coupler and the disulfide can be easily carried out, e.g., in a molar ratio of about 1:1 to 1:10 of the coupler to the disulfide, in the presence of an alkali at a temperature of about 0 to 150° C for a short period of time to provide a desired product in a high yield. Any magenta color image forming coupler can be used without limitation as the four-equivalent coupler, as long as the coupler has one or two hydrogen atoms at the coupling position. The alkali catalyst used is not particularly limited and any base which can dissociate the four-equivalent coupler, including an inorganic base such as sodium hydroxide, potassium hydroxide, sodium carbonate, sodium bicarbonate, sodium alcoholate, etc. and an organic base such as triethylamine, 1,4-diazabiscyclo[2,2,2]-octane, can be used. The amount of the alkaline catalyst can range from about 0.1 to 5 mol per mol, preferably 0.5 to 1 mol, of the four-equivalent coupler. The desired compound can be obtained without using an alkali catalyst appropriately selecting a reaction solvent, e.g., aprotic polar solvent such as dimethylformamide, dimethyl sulfoxide, hexamethylphosphotriamide and the like.

The reaction solvent which can be used is not particularly limited and a polar solvent, a non-polar solvent, a protic solvent, and an aprotic solvent can be used. Preferred solvents are carboxylic acid solvents for example, acetic acid, propionic acid; halogenated hydrocarbon solvents for example, methylene chloride, chloroform, carbon tetrachloride; aromatic solvents, for example, benzene, xylene, pyridine; alcoholic solvents for example, methanol, ethanol, propanol, n-butanol, 10% aqueous ethanol; aprotic polar solvents, for example, dimethylformamide, dimethyl sulfoxide, hexamethylphosphotriamide; and the like. A preferred temperature range for the reaction can be from about 20° to 100° C. The reaction time can be varied over a wide range depending on the reaction temperature and the solvent used, but generally the reaction time ranges from about 5 minutes to about 24 hours. After the reaction is completed, as indicated by thin layer chromatography that the four-equivalent coupler of a starting material is consumed, the desired product can be obtained using conventional extraction, drying, concentration and crystallization techniques.

The disulfide which is one of the starting materials can be easily prepared in a well known manner by oxidizing a mercapto compound represented by the formula

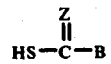

wherein B and Z each have the same meaning as defined previously, with an appropriate oxidizing agent for example, iodine, hydrogen peroxide, calcium oxychloride, etc.

Typical examples of the synthesis of the magenta couplers of the present invention are illustrated below, but these examples are not to be construed limiting the present invention. Unless otherwise indicated herein, all parts, percents, ratios and the like are by weight.

SYNTHESIS EXAMPLE 1

Preparation of [1-(2,4,6-Trichlorophenyl)-3-{2-chloro-4-[α-(2,4-di-tert-amylphenoxy)butyramido]anilino}-5-oxo-2-pyrazolin-4-yl]-N,N-dimethylaminecarbodithioate (Coupler (1)

14 g of 1-(2,4,6-Trichlorophenyl)-3{2-chloro-4-[α-(2,4-di-tert-amylphenoxy)butyramido]anilino}-5-oxo-2-pyrazoline was added to 100 ml of a 10% aqueous ethanol solution (water: ethanol = 1:9 by volume) and to which 4.8 g of tetramethylthioulamedisulfide and 1.5 g of potassium carbonate was added and the mixture was refluxed by heating for 30 minutes. After determination that the starting material was completely consumed by thin layer chromatography, the reaction mixture was rapidly cooled with running water. To the mixture 200 ml of ethyl acetate was added and the mixture washed with water, neutralized with a small amount of acetic acid, and washed repeatedly with water. The ethyl acetate layer was dried with anhydrous sodium sulfate, concentrated under reduced pressure to remove the solvent and the residue was recrystallized with a mixture of acetonitrile and ethyl acetate (10:1 by volume) to provide 10.4 g of Coupler (1) having a melting point of 132 to 135° C.

Elemental Analysis: Calculated for $C_{38}H_{45}N_5S_2O_3Cl_4$ (%); H: 5.46; C: 55.2; N: 8.49. Found (%); H: 5.63, C: 55.0; N: 8.69.

SYNTHESIS EXAMPLE 2

Preparation of S-{1-[α-(2,4-Di-tert-amylphenoxy)butyramido]-phenyl-3-methyl-5-oxo-2-pyrazolin-4-yl}-ethyldithiocarbonate (Coupler (7))

A mixture of 8.9 g of 1-[α-(2,4-di-tert-amylphenoxy)-butyramido]phenyl-3-methyl-5-oxo-2-pyrazoline, 2.4 g of di(ethoxythiocarbonyl) disulfide and 1.4 g of potassium carbonate was added to 100 ml of dimethylformamide and the mixture was stirred at 25° C for 4 hours. After the completion of the reaction, 200 ml of ethyl acetate was added and the product was worked-up in the same manner as Synthesis Example 1, crystallized with acetonitrile to provide 4.2 g of Coupler (7) having a melting point of 165° to 168° C.

Elemental Analysis: Calculated for $C_{32}H_{45}N_3O_4S_2$ (%); H: 7.51; C: 64.1; N: 7.01. Found (%); H: 7.43; C: 63.97; N: 7.11.

The couplers which can be used in the present invention can be clearly distinguished from conventionally known two-equivalent magenta couplers described above in their chemical structures. The couplers of the present invention are chemically stable and the synthesis of the couplers of the present invention is very easy as is apparent from the above syntheses examples.

The coupler of the present invention is a two-equivalent coupler which theoretically requires only two equivalents of silver halide, as an oxidizing agent, for forming one molecule of a dye. The silver halide required can be reduced to about half of that required in using a prior art four-equivalent pyrazolone type coupler, thus not only halving the silver halide contained in a light-sensitive material and reducing the cost of production of the light-sensitive material, but also reducing the light scattering due to the silver halide grains in the emulsion and improving the sharpness of the image.

The magenta coupler used in the present invention can be converted into an azomethine dye in a high yield by the oxidizing coupling reaction using an exposed silver halide as an oxidizing agent. Some of the four-equivalent couplers used in the prior art have a low conversion yield into the dye, since the leuco dye produced as an intermediate product gives rise to side reactions such as azine ring formation. On the contrary, the magenta coupler used in the present invention can be converted into an azomethine dye in a high yield, since the reaction does not progress through such a reactive intermediate product. Consequently, in the color photographic light-sensitive material according to the present invention, it is possible to reduce the quantity of the magenta forming coupler, to reduce the amount of the silver halide and to reduce the thickness of the emulsion layer. Thus, it is easy to reduce the cost of the light-sensitive material, to improve the sharpness and to promote development.

The magenta coupler used in the present invention has a strong coupling activity for an oxidizing aromatic primary amine color developing agent and rapidly removes the oxidized product of the developing agent formed during color development, so that the development of the silver halide emulsion is accelerated.

With the magenta coupler used in the present invention, the process of forming a dye is completed in a color developing bath and it is not necessary to use thereafter a bleaching bath containing a strong oxidizing agent such as potassium ferricyanide or potassium dichromate. Thus a treatment with a blixing bath containing a silver complex salt forming agent and a weak oxidizing agent such as a ferric chelate of EDTA or a bleaching bath containing a ferric salt (for example, ferric chloride) is possible and, consequently, it is easy to shorten the overall time for the color processing as well as to solve the problem of environmental pollution in waste processing solution discharge.

The magenta coupler used in the present invention in which the coupling position is substituted is inactivated by carbonyl compounds such as aldehydes and ketones to a lesser extent, while the coupling-position-unsubstituted magenta coupler used in the prior art, in particular, in an emulsion layer is changed into a compound of low color forming reactivity such as a methylol or methylene bis-compound by formaldehyde in the air, which often does not provide sufficient color forming property during color development. One feature of the color photographic light-sensitive material according to the present invention is that the material is hardly influenced by such chemicals.

The coupling-position-substituted magenta coupler used in the present invention has the advantages when used for conventional color photographic light-sensitive materials as described in the Examples set forth hereinafter, e.g., the stability in an emulsion layer with the passage of time is high and, in particular, the color forming property is reduced to a lesser extent even after the passage of time at low temperature or under high humidity conditions, as compared with the above described known couplers. The retention of the characteristic of a fresh film on storage is one of the most important factors as to the assessment of the properties of a color photographic light-sensitive material.

Moreover, it has been found that the color developed dye image formed from the magenta coupler of the present invention has superior heat resistance than that formed from coupling-position-unsubstituted couplers and, even in comparision with the foregoing known coupler in which the 4-position in the same pyrazolone nucleus is substituted, the coupler of the present invention has a higher heat resistance.

The two-equivalent magenta coupler of this invention can be used together with the magenta couplers as described in, for instance, U.S. Pat. Nos. 2,439,089; 2,369,489; 2,600,788; 3,558,319; 2,311,081; 3,419,391; 3,214,437; 3,006,759; 2,725,292; 3,408,194; 2,908,573; 3,519,429; 3,615,506; 3,432,521; 3,152,896; 3,062,653; 3,582,322; 2,801,171; 3,311,476; British Pat. No. 956,261; Japanese Patent Publication Nos. 2016/1969 and 19032/1971; Japanese Patent Application Nos. 114445/1972, 56050/1973; 45971/1973; 21454/1973; 108798/1973; and 114446/1972, in which the amount of these other magenta couplers employed with the two equivalent magenta couplers of the invention, in general, ranges from about 5 to 80 mole % based on the total amount of the magenta couplers employed; with the magenta-colored couplers as described in U.S. Pat. Nos. 2,983,608; 2,455,170; 2,725,292; 3,005,712; 3,519,429; and 2,688,539; British Pat. Nos. 800,262 and 1,044,778; and Belgian Pat. No. 676,691, in which these magenta couplers are incorporated in an amount from about 2 to 20 mole % to the total amount of the magenta couplers employed; with the so-called development inhibitor releasing type couplers capable of imagewise releasing development inhibiting compounds at development, such as, for instance, the monothio type couplers as described in U.S. Pat. Nos. 3,227,550 and 3,227,554 and British Pat. No. 953,454, the o-aminophenylazo type couplers as described in U.S. Pat. No. 3,148,062, and the couplers as described in Japanese Pat. Publication No. 8750/1972 and German Patent Application (OLS) No. 2,163,811 with these couplers generally being incorporated in an amount from about 2 to 20 mole % to the total amount of the magenta couplers employed and also, with as described in U.S. Pat. No. 3,297,445 and British Pat. No. 1,058,606, the hydroquinone releasing development inhibiting compounds, which can be employed therewith in an amount from about 2 to 20 mole % to the total amount of the magenta couplers employed.

One or more of the above described compounds such as the magenta couplers and the like can be incorporated in the same layer or the same compound can be incorporated in one or more layers, in order to achieve the characteristics required in the photographic light-sensitive material. In general, the coupler of the present invention can be coated on a support in an amount ranging from about $1 \times 10^{-4}$ to $5 \times 10^{-3}$ mole/m$^2$, preferably $3 \times 10^{-4}$ to $2 \times 10^{-3}$ mole/m$^2$.

The coupler of the present invention also can be used in a developer solution. In such case a suitable amount of the coupler ranges from about 0.2 to 50 g, preferably 0.5 to 10 g, per liter of the developer solution.

The coupler of the present invention is advantageously used in combination with a green-sensitive silver halide emulsion. For the purpose of improving the fastness to light of the magenta dye formed in an emulsion layer or an adjacent layer thereto, or preventing yellowing or print-out of the coupler remaining in an unexposed portion or color stain, the photographic lightsensitive material used in the present invention advantageously can contain a p-substituted phenol derivative. Particularly suitable p-substituted phenol derivatives can be selected from one or more of the hydroquinone derivatives described in U.S. Pat. Nos. 2,360,290; 2,418,613; 2,675,314; 2,701,197; 2,704,713; 2,710,801; 2,728,659; 2,732,300; 2,735,765 and 2,816,028, the gallic acid derivatives described in U.S. Pat. Nos. 3,457,079 and 3,069,262 and Japanese Patent Publication No. 13496/1968, the p-alkoxyphenols described in U.S. Pat. No. 2,735,765 and Japanese Patent Application (OPI) No. 4738/1972 and the p-oxyphenol derivatives described in U.S. Pat. Nos. 3,432,300; 3,573,050; 3,574,627; 3,764,337 and 3,698,909 and Japanese Patent Publication No. 20977/1974.

Silver halide emulsions are usually prepared by mixing a solution of a water-soluble silver salt, for example, silver nitrate with a water-soluble halide, for example, potassium bromide in the presence of a water-soluble polymer, for example, gelatin. In addition to silver chloride and silver bromide, mixed silver halides such as silver chlorobromide, silver iodobromide and silver chloroiodobromide can be employed in the present invention. The silver halide grains can be prepared according to conventional methods, including the so-called single jet method, double jet method and controlled double jet method. Mixtures of two or more silver halide photographic emulsions which are prepared separately can also be used. The silver halide grains can have a homogeneous crystal structure, can have a layered structure in which the interior differs from the outer layer, or can be the so-called conversion-type silver halide grains as described in British Pat. No. 635,841 and U.S. Pat. No. 3,622,318. Silver halide grains which form a latent image predominantly on the surface of the grains or predominantly in the interior of the grains can also be used. These photographic emulsions can be prepared by various known methods such as an ammonia method, a neutral method and an acid method.

The silver halide emulsion described above can be chemically sensitized using conventional methods. Specific examples of suitable chemical sensitizers include, for example, gold compounds such as chloroaurates and gold trichloride as described in U.S. Pat. Nos. 2,399,083, 2,540,085, 2,597,856 and 2,597,915, salts of a noble metal, such as platinum, palladium, iridium, rhodium and ruthenium, as described in U.S. Pat. Nos. 2,448,060, 2,540,086, 2,566,245, 2,566,263 and 2,598,079, sulfur compounds capable of forming silver sulfide by reacting with a silver salt, such as those described in U.S. Pat. Nos. 1,574,944, 2,410,689, 3,189,458 and 3,501,313, stannous salts, amines, and other reducing compounds such as those described in U.S. Pat. Nos. 2,487,850, 2,518,698, 2,521,925, 2,521,926, 2,694,637, 2,983,610 and 3,201,254, and the like.

Examples of the hydrophilic collids which can be used as a vehicle or binder for the silver halide grains include, for example, gelatin, colloidal albumin, casein, a cellulose derivative such as carboxymethylcellulose and hydroxyethylcellulose, agar, sodium alginate, a starch derivative, a synthetic hydrophilic colloid such as polyvinyl alcohol, poly-N-vinyl-pyrrolidone, a polyacrylic acid copolymer and polyacrylamide, or the derivatives or partially hydrolyzed products thereof. If desired, a compatible mixture of these colloids can also be used. Of these colloids, gelatin is most commonly employed. The gelatin can be replaced partially or completely by a synthetic polymer, by the so-called gelatin derivatives such as those prepared by reacting or modifying the amino, imino, hydroxy or carboxy groups contained, as functional groups, in the gelatin molecule with a compound having a group capable of reacting with the above-described groups, or a graft gelatin such as those prepared by grafting another polymer chain on the gelatin molecule.

The photographic emulsion can be spectrally sensitized or super-sensitized, if desired, using a cyanine dye such as the cyanine, merocyanine, carbocyanine or styryl dyes, individually or in combination. These spectral sensitization techniques are well known and are described, for example, in U.S. Pat. Nos. 2,688,545, 2,912,329, 3,397,060, 3,615,635 and 3,628,964, British Pat. Nos. 1,195,302, 1,242,588 and 1,293,862, German Patent Application (OLS) Nos. 2,030,326 and 2,121,780 and Japanese Patent Publication Nos. 4936/1968 and 14030/1969. The sensitizers can be chosen as desired depending on the spectral range, sensitivity, and the like due to the purpose and uses of the photographic materials to be sensitized.

Various kinds of conventional stabilizers or antifogging agents can be added to the photographic emulsion described above in order to prevent a reduction in the sensitivity or a formation of fog during preparation, storage or processing. A wide variety of such compounds are known such as heterocyclic compounds, mercury-containing compounds, mercapto compounds or metal salts, including 4-hydroxy-6-methyl-1,3,3a,7-tetrazaindene, 3-methylbenzothiazole and 1-phenyl-5-mercaptotetrazole.

The photographic emulsion can be hardened using conventional methods. Examples of suitable hardeners include, for example, an aldehyde type compound such as formaldehyde and glutaraldehyde; a ketone compound such as diacetyl and cyclopentanedione; a reactive halogen-containing compound such as bis(2-chloroethylurea), 2-hydroxy-4,6-dichloro-1,3,5-triazine and those described in U.S. Pat. Nos. 3,288,775 and 2,732,313 and British Pat. Nos. 974,723 and 1,167,207; divinylsulfone; 5-acetyl-1,3-diacryloyl-hexahydro-1,3,5-triazine; the compounds described in U.S. Pat. Nos. 3,635,718, and 3,232,763, British Pat. No. 994,869, U.S. Pat. Nos. 2,732,316, 2,586,168, 3,103,437, 3,017,280, 2,983,611, 2,725,294, 2,725,295, 3,100,704, 3,091,537, 3,321,313, 3,543,292, etc.

The photographic emulsion described above can also contain one or more surface active agents. These surface active agents are used as a coating aid, a dispersing agent, a sensitizer, an agent for improving photographic properties, an antistatic agent or an adhesion preventing agent. The surface active agents can be classified as natural surface active agents such as saponin; nonionic surface active agents such as alkylene oxides, glycerols and glycidols; cationic surface active agents such as higher alkylamines, quaternary ammonium salts, heterocyclic compounds such as pyridine and the like, phosphoniums or sulfoniums; anionic surface active agents containing an acid group such as a carboxylic acid group, a sulfonic acid group, a phosphoric acid group, a sulfuric acid ester group or a phosphoric acid ester group; amphoteric surface active agents such as amino acids, aminosulfonic acids, aminoalcohol sulfuric acid esters or aminoalcohol phosphoric acid esters. Some examples of those surface active agents which can be used are described, for example, in U.S. Pat. Nos. 2,271,623, 2,240,472, 2,288,226, 2,739,891, 3,068,101, 3,158,484, 3,201,253, 3,210,191, 3,294,540, 3,415,649, 3,441,413, 3,442,654, 3,475,174 and 3,545,974, German Patent Application (OLS) No. 1,942,665, British Pat. Nos. 1,077,317 and 1,198,450, and the like.

The magenta coupler of the present invention can be used in a multilayer color photographic light-sensitive material containing a yellow coupler and a cyan coupler. An open-chain diketomethylene type compound is conventionally used as a yellow coupler. Examples of such compounds are described, for example, in U.S. Pat. Nos. 3,341,331, 3,253,924, 3,384,657, 2,778,658, 2,908,573, 3,227,550, 2,875,057 and 3,551,155, German Patent Application (OLS) No. 1,547,868, U.S. Pat. Nos. 3,265,506, 3,582,322 and 3,725,072, German Patent Application (OLS) No. 2,162,899, U.S. Pat. Nos. 3,369,895, 3,227,155, 3,447,928, 3,415,652, and 3,408,194, German Patent Application (OLS) Nos. 2,057,941, 2,213,461, 2,219,917, 2,261,361 and 2,263,875, and the like.

Typical examples of suitable yellow couplers are the following compounds:

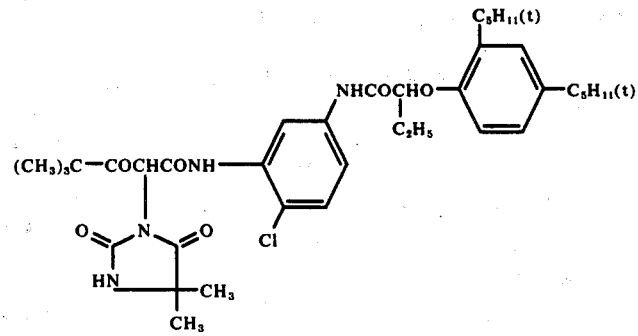

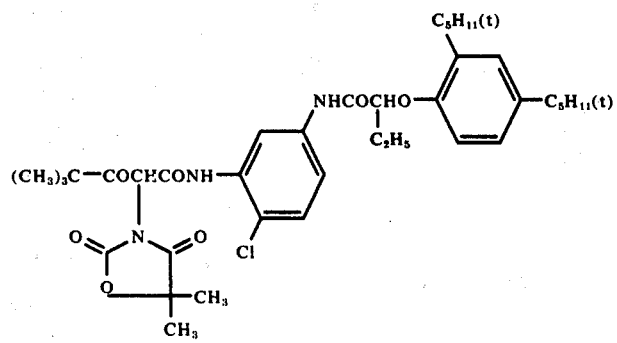

-continued

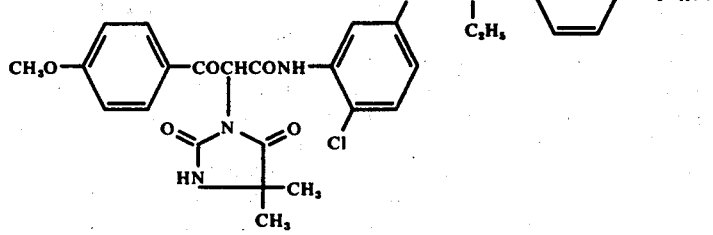

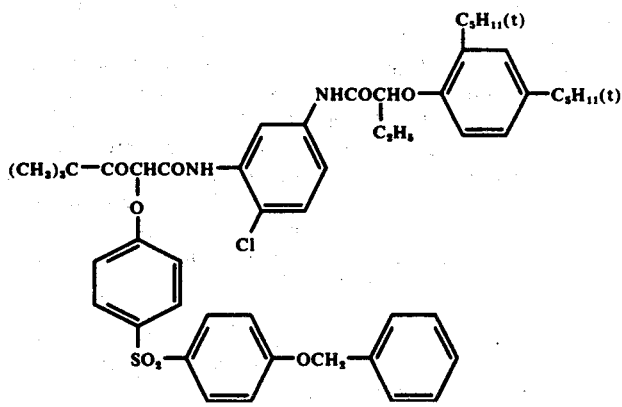

A phenol or naphthol derivative is conventionally used as a cyan coupler. Examples of such compounds are described, for example, in U.S. Pat. Nos. 2,369,929, 2,474,293, 2,908,573, 3,619,196, 3,253,294, 3,227,550, 3,419,390, 3,476,563, 2,698,794, 2,895,826, 3,311,476, 3,458,315, 2,423,730, 2,801,171, 3,046,129, 3,516,831, 2,772,162, 3,560,212, 3,582,322, 3,591,383, 3,386,301, 3,632,347, 3,652,286, 3,779,763, 2,434,272, 2,706,684, 3,034,892, and 3,583,971, German Patent Application (OLS) Nos. 2,163,811 and 2,207,468, Japanese Patent Publication Nos. 28836/1970 and 27563/1964, Japanese Patent Application No. 33238/1973, and the like.

Typical examples of suitable cyan couplers are the following compounds:

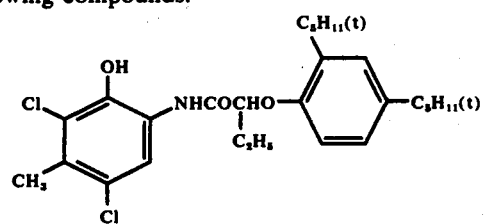

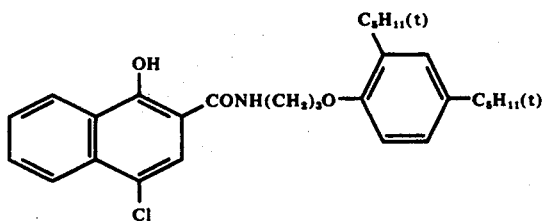

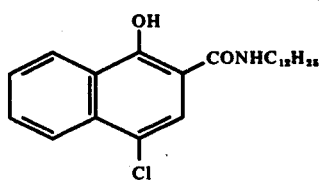

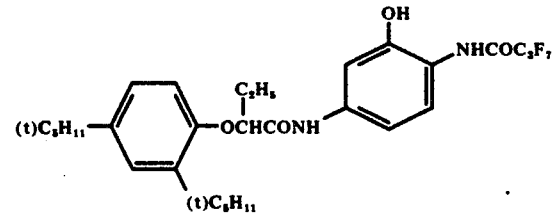

The color photographic light-sensitive material according to the present invention can contain, in a protective layer, an intermediate layer, an emulsion layer or a backing layer, an ultraviolet absorbing agent as described, for example, in U.S. Pat. Nos. 2,685,512, 2,739,888, 2,784,087, 3,253,921, 3,533,794, 3,738,837 and 3,754,919, and the like.

The photographic emulsion can be coated on a substantially planar material which does not undergo severe dimensional change during processing including a rigid support such as glass, metal or ceramics, or a flexible support as desired. Representative flexible supports include those generally used for photographic light-sensitive materials, such as a cellulose nitrate film, a cellulose acetate film, a cellulose acetate butyrate film, a cellulose acetate propionate film, a polystyrene film, a polyethylene terephthalate film, a polycarbonate film, a laminate of these polymers, a thin glass film and a paper. A baryta coated paper, a paper which is coated or laminated with an α-olefin polymer, particularly those obtained from a monomer having from 2 to 10 carbon atoms such as polyethylene, polypropylene and ethylene-butene copolymers, and a synthetic resin film in which the adhesiveness to other polymers and the printing properties are improved by roughening its surfaces, such as is described in Japanese Patent Publication No. 19068/1972, can also be used to advantage as a support. A suitable amount of silver halide which can be coated ranges from about $5 \times 10^{-5}$ to $10^{-1}$ mol/m$^2$.

These supports can be transparent or opaque, depending on the purpose of the photographic materials. Colored transparent supports which contain a dye or a pigment can also be used.

Examples of opaque supports include films produced by incorporating into a transparent film a dye or a pigment such as titanium oxide or surface-treated synthetic resin films such as those described in Japanese Patent Publication No. 19068/1972, as well as intrinsically opaque materials such as paper. Highly light-shielding papers and synthetic resin films containing, for example, carbon black or dyes can also be employed. When the adhesion between a support and a photographic layer is unsatisfactory, a subbing layer which adheres well to both the support and the photographic layer can be provided on the support. The surfaces of the supports can also be pre-treated by corona discharge, a UV radiation treatment, a flame treatment and the like in order to further improve the adhesiveness.

The color photographic light-sensitive materials of the present invention are, after exposure, subjected to a color processing to form dye images. The color processing includes basically a color development step, a bleaching step and a fixing step. Each step can be carried out individually or two or more steps can be combined into one step where a processing solution having two or more of these functions is used. One example of such a combined bath is a blix solution. Also, each step can be separated into two or more steps. For example, a process comprising a color development step, a first fixing step and a blixing step can be used. The color processing can further include a pre-hardening step, a neutralization step, a first development (black and white development) step, a stabilizing step, a washing step, and the like, if desired. The temperature of processing can be varied depending on the photographic light-sensitive material, the color processing method, and the like. In general, a temperature above about 18° C is used, although a temperature below about 18° C can also be used. A temperature ranging from about 20 to 60° C, recently about 30 to 60° C, is conventionally used. These steps need not necessarily be conducted at the same temperature.

A color developer solution is an alkaline solution having a pH of higher than about 8, preferably from 9 to 12, and containing, as a developing agent, a compound whose oxidized product is capable of forming a colored compound when reacted with a color forming agent, i.e., a color coupler.

The developing agent described above includes a compound capable of developing an exposed silver halide and having a primary amino group on an aromatic ring, and a precursor which can form such compound. Preferred typical examples of these developing agents are, for example, 4-amino-N,N-diethylaniline, 3-methyl-4-amino-N,N-diethylaniline, 4-amino-N-ethyl-N-α-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline, and the salts thereof (for example, the sulfates, the hydrochlorides, the sulfites, the p-toluene sulfonates, and the like). Other developing agents such as those described in U.S. Pat. Nos. 2,193,015 and 2,592,364, Japanese Patent Application (OPI) No. 64933/1973, and L. F. A. Mason, *Photographic Processing Chemistry*, pages 226 to 229, Focal Press, London (1966). Also, 3-pyrazolidones can be used together with these developing agents.

The color developer solution can optionally contain various additives. Typical examples of such additives include alkaline agents (for example, the hydroxides, carbonates or phosphates of the alkali metals or ammonia); pH-adjusting agents or buffers (for example, weak acids such as acetic acid, boric acid, etc., weak bases, or the salts thereof); developing accelerators (for example, various pyridinium compounds or cationic compounds such as those described in U.S. Pat. Nos. 2,648,604 and 3,671,247; potassium nitrate; sodium nitrate; condensation products of polyethylene glycol, and the derivatives thereof such as those described in U.S. Pat. Nos. 2,533,990, 2,577,127 and 2,950,970; nonionic compounds such as polythioethers represented by those described in British Pat. Nos. 1,020,033 and 1,020,032; polymeric compounds having sulfite ester groups such as those described in U.S. Pat. No. 3,068,097; organic amines such as pyridine and ethanolamine; benzyl alcohol; hydrazines and the like); anti-fogging agents (for example, alkali metal bromides, alkali metal iodides, nitrobenzimidazoles such as those described in U.S. Pat. Nos. 2,496,940 and 2,656,271, mercaptobenzimidazole, 5-methyl-benzotriazole, 1-phenyl-5-mercaptotetrazole, compounds for use in rapid processing solutions such as those described in U.S. Pat. Nos. 3,113,864, 3,342,596, 3,295,976, 3,615,522 and 3,597,119, thiosulfonyl compounds such as those described in British Pat. No. 972,211, phenazine-N-oxides such as those described in Japanese Patent Publication No. 41675/1971, those described in *Kagaku Shashin Binran (Manual of Scientific Photography)*, Vol. II, pages 29 to 47, and the like); stain or sludge preventing agents such as those described in U.S. Pat. Nos. 3,161,513 and 3,161,514 and British Pat. Nos. 1,030,422, 1,144,481 and 1,251,558; interlayer-effect accelerators disclosed in U.S. Pat. No. 3,536,487; preservatives (for example, sulfites, bisulfites, hydroxylamine hydrochloride, formsulfite, alkanolamine-sulfite adducts, etc.), and the like.

After color development, the light-sensitive material of the present invention is subjected to a bleaching step in a conventional manner. The bleaching step can be carried out individually or in combination with a fixing step. The bleaching solution can contain a fixing agent to form a blix bath, if desired. Many kinds of compounds are known as a bleaching agent. Of these compounds, ferricyanides; bichromates; water-soluble cobalt(III) salts; water-soluble copper(II) salts; water-soluble quinones; nitrosophenols; complex salts of a polyvalent cation such as iron(III), cobalt(III), copper(II) and an organic acid, for example, an aminopolycarboxylic acid such as ethylenediamine tetraacetic acid, nitrilotriacetic acid, iminodiacetic acid, N-hydroxyethylethylenediaminetriacetic acid, etc., malonic acid, tartaric acid, malic acid, diglycolic acid and dithioglycolic acid, etc.; a copper complex of 2,6-dipicolinic acid; peracids such as alkylperacids, persulfates, permanganates and peroxides; hypochlorites; chlorine; bromine; and the like can be suitably used, individually or in combination. To the bleaching solution, bleaching accelerators such as those described in U.S. Pat. Nos. 3,042,520 and 3,241,966, Japanese Patent Publication Nos. 8506/1970 and 8836/1970 and other various additives can be added.

The formation of dye images according to the present invention can be achieved in light-sensitive materials of various forms. In one form, a light-sensitive material having a silver halide emulsion layer containing a diffusion resistant coupler on a support is processed with an alkaline developer solution containing an aromatic primary amine color developing agent to retain a water insoluble or diffusion resistant dye in the emulsion layer. In another form, a light-sensitive material having a silver halide emulsion layer in combination with a diffusion resistant coupler on a support is processed with an alkaline developer solution containing an aromatic primary amine color developing agent to form a dye soluble in an aqueous medium and diffusible and then transferred to another receiving layer of a hydrophilic colloid. This is a diffusion transfer color system. In still another form, a light-sensitive material having a silver halide emulsion layer is processed with an alkaline developer solution containing an aromatic primary amine color developing agent and a coupler dissolved therein to retain a water insoluble or diffusion resistant dye in the emulsion layer. This is a coupler-in-the-developer type system. For example, Couplers (6) and (13) described above can be used for the second form, Coupler (11) described above can be used for the third form, while the others described above can be used for the first form.

The color photographic light-sensitive material of the present invention includes a color negative film, a color positive film, a color reversal film, a color printing paper and any other kind color photographic light-sensitive materials, for example, a color direct positive light-sensitive material, a light-sensitive material for a color diffusion transfer process, a monochromatic light-sensitive material, and the like.

Also, the photographic light-sensitive material containing the coupler of the present invention can be suitably applied to a method in which developed silver formed by color development is halogenation-bleached and then color developed again to increase the amount of dye formed, such as described, for example, in U.S. Pat. Nos. 2,439,901, 2,623,822, 2,814,565 and 3,372,028, or to a method in which silver halide content in a light-sensitive material is reduced using a color intensification method as described in Japanese Patent Application (OPI) No. 9728/1973.

Some of the advantageous results obtained according to the present invention are described below 1. The amount of silver required to provide a certain magenta color image density can be reduced, thus providing the ability to reduce the thickness of the light-sensitive layer containing the coupler and improving the sharpness of the image.

2. The heat resistance of the magenta color image formed is improved by using the coupler of the present invention.

3. A reduction in the cost of production of the light-sensitive material is achieved by using a reduced amount of silver halide.

4. Magenta couplers which are more stable to chemical compounds such as formaldehyde or acetone are provided.

5. Couplers having a high coupling reactivity are provided.

6. A color image having a lower fog and stain extent and superior photographic properties is obtained.

7. A silver halide color photographic light-sensitive material having a good stability under storage is obtained by using the coupler of the present invention.

8. The conversion yield of the coupler into the dye is improved by using the coupler of the present invention.

The present invention will be further explained by reference the following examples.

EXAMPLE 1

A mixture of 24.5 g of Coupler (2) of the present invention, 24 ml of dioctyl butyl phosphate and 60 ml of ethyl acetate was heated at 60° C and the resulting solution was added to 250 ml of an aqueous solution containing 25 g of gelatin and 0.75 g of sodium dodecylbenzenesulfonate at 60° C, followed by vigorous mechanical stirring using a homogenizer, thus obtaining a coupler dispersion. The resulting coupler dispersion was mixed with 200 g of a photographic emulsion containing $11.2 \times 10^{-2}$ mol of silver chlorobromide (silver bromide: 45 mol%; silver chloride: 55 mol%) and 20 g of gelatin and, then 10 ml of a 3% acetone solution of triethylenephosphoramide, as a hardener, was added thereto and the final pH was adjusted to 6.5. The mixture was coated onto a cellulose triacetate film base in a dry thickness of 4.5 microns (Film A). This film contained, per m², $1.55 \times 10^{-3}$ mol of the coupler and $6.2 \times 10^{-3}$ mol of silver chlorobromide.

For comparison, 18.8 g of 1-(2,4,6-trichlorophenyl)-3- 3-[α-(2,4-di-tert-amylphenoxy)butyramido]benzamido -5-oxo-2-pyrazoline (Comparison Coupler A) as a corresponding comparison coupler in which the coupling position was unsubstituted, was dispersed, in place of the above described coupler in a manner similar to the above described coupler, mixed with 400 g of the same emulsion as described above and coated onto a film in a dry thickness of 5.1 microns (Film B). This film contained, per m², $1.57 \times 10^{-3}$ mol of the coupler and $12.6 \times 10^{-3}$ mol of silver chlorobromide.

These films were subjected to stepwise exposure and then to the following processing:

| Color Processing Step | | |
|---|---|---|
| 1. Color Development | 21° C | 12 min. |
| 2. Water Washing | " | 30 sec. |
| 3. First Fixing | " | 4 min. |
| 4. Water Washing | " | 4 min. |
| 5. Bleaching | " | 8 min. |
| 6. Water Washing | " | 4 min. |
| 7. Second Fixing | " | 6 min. |
| 8. Water Washing | " | 6 min. |
| Color Developer Solution | | (pH 10.7) |
| Sodium Hexametaphosphate | | 2 g |
| Sodium Sulfite (anhydrous) | | 2 g |
| Benzyl Alcohol | | 5 ml |
| Sodium Carbonate (monohydrate) | | 27.5 g |
| Potassium Bromide | | 0.5 g |
| Hydroxylamine Sulfate | | 2.5 g |
| N-Ethyl-N-(β-methanesulfonamidoethyl)-3-methyl-4-aminoaniline Sesquisulfate | | 2.5 g |
| Water to make | | 1 liter |
| Fixing Solution | | (pH 4.5) |
| Sodium Thiosulfate (hexahydrate) | | 80 g |
| Sodium Sulfite (anhydrous) | | 5 g |
| Borax | | 6 g |
| Glacial Acetic Acid | | 4 ml |
| Potassium Alum | | 7 g |
| Water to make | | 1 liter |

-continued

| Bleaching Solution | (pH 7.2) |
|---|---|
| Potassium Ferricyanide | 100 g |
| Potassium Bromide | 5 g |
| Boric Acid | 10 g |
| Borax | 5 g |
| Water to make | 1 liter |

After the processing, the optical density of these films were measured with green light to obtain the photographic properties as shown in Table 1 below. A clear color image was obtained having an absorption maximum of 542 m$\mu$.

Table 1

| Film | Coupler | Coating Amount Coupler (mol/m$^2$) | Coating Amount AgX (mol/m$^2$) | AgX/ Coupler (molar ratio) | Thickness ($\mu$) | Fog | Gamma | Relative Sensitivity* | Maximum Color Density |
|---|---|---|---|---|---|---|---|---|---|
| A | (2) | 1.55×10$^{-3}$ | 6.2×10$^{-3}$ | 4 | 4.1 | 0.03 | 2.98 | 100 | 3.45 |
| B | A | 1.57×10$^{-3}$ | 12.6×10$^{-3}$ | 8 | 5.1 | 0.02 | 2.18 | 93 | 2.43 |

*Relative sensitivity means the quantity of exposure necessary for providing a density of fog + 0.1

As is evident from the results in Table 1, the coupler of the present invention provided a higher sensitivity and gradation as well as a maximum color density, even when the silver halide/coupler ratio decreased to about 1/2. The above results demonstrate that in using the coupler of the present invention, the quantity of developed silver necessary for obtaining a color image having a certain density can be reduced. That is, the quantities of the coupler and coated silver halide necessary for obtaining a certain maximum color density can be reduced and the developing time can be shortened.

EXAMPLE 2

Using Film A and Film B as described in Example 1, the following processing was carried out:

| Color Processing Step | | |
|---|---|---|
| 1. Color Development | 30° C | 4 min. |
| 2. Blixing | " | 2 min. |
| 3. Water Washing | " | 2 min. |
| 4. Stabilizing Bath | " | 2 min. |

The photographic properties of the thus obtained films are shown in Table 2 below.

Moreover, as to the Stabilizing Bath, two kinds of stabilizing baths, i.e., Stabilizing Bath (a) not containing any formaldehyde and Stabilizing Bath (b) containing 1% of a 40% formaldehyde aqueous solution were prepared. The films were treated respectively with these baths, allowed to stand at 80° C for one week and the ratio of the decrease in the density based on the initial density was measured. The results obtained are shown in Table 3 below.

| Color Developer Solution | (pH 10.2) |
|---|---|
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (nitrate) | 0.02 g |
| Sodium Hydroxide | 4 g |
| Benzyl Alcohol | 15.8 g |
| Diethylene Glycol | 20 ml |
| 4-(N-Ethyl-N-$\beta$-methanesulfonamidoethyl) amino-2-methylaniline Sesquisulfate | 8 g |
| Water to make | 1 liter |
| Blixing Solution | (pH 6.9) |
| Ferric Ethylenediaminetetraacetate | 45 g |
| Ammonium Thiocyanate | 10 g |
| Sodium Sulfite | 10 g |
| Ammonium Thiosulfate (60% aq. soln.) | 100 ml |
| Sodium Ethylenediaminetetraacetate | 5 g |
| Water to make | 1 liter |
| Stabilizing Bath (a) | |
| Tartaric Acid | 10 g |
| Zinc Sulfate | 10 g |
| Sodium Metaborate | 20 g |
| Water to make | 1 liter |
| Stabilizing Bath (b) | |
| Tartaric Acid | 10 g |
| Zinc Sulfate | 10 g |
| Sodium Metaborate | 20 g |
| Formaldehyde (40% aq. soln.) | 10 g |
| Water to make | 1 liter |

Table 2

| | | Photographic Property (Stabilizing Bath (a)) | | |
|---|---|---|---|---|
| Film | Coupler | Fog | Gamma | Maximum Color Density |
| A | (2) | 0.04 | 2.91 | 3.45 |
| B | A | 0.03 | 2.21 | 2.35 |

Table 3

| | | Durability of Color Image (80° C, standing for one week) | | |
|---|---|---|---|---|
| Film | Stabilizing Bath | Initial Density | | |
| | | 0.5 (%) | 1.0 (%) | 2.0 (%) |
| A | a | 12 | 8 | 6 |
| | b | 11 | 7 | 4 |
| B | a | 55 | 41 | 10 |
| | b | 13 | 8 | 4 |

The results in Table 2 show that the use of Film A results in sufficient photographic properties even though a strong oxidizing agent is not used as in the processing of Example 1 and that Film A has superior properties to Film B. The results in Table 3 show that Film A provide sufficient heat durability even though it was not subjected to a stabilizing bath treatment containing formaldehyde as in the prior art.

EXAMPLE 3

Onto a baryta paper resin-coated with polyethylene were coated, as a first layer, a blue-sensitive silver chlorobromide emulsion containing $\alpha$-pivaloyl-$\alpha$-(2,4-dioxo-5,5-dimethyloxazolidin-3-yl)-2-chloro-5-[$\alpha$-(2,4-di-tert-amylphenoxy)butyramido]acetanilide in a dry thickness of 3.0 microns (coupler coated amount: 1.18 × 10$^{-3}$ mol/m$^2$; silver coated amount: 3.53 × 10$^{-3}$ mol/m$^2$; silver bromide: 70 mol%, silver chloride: 30 mol%) and further, as a second layer, gelatin containing 2-tert-octylhydroquinone in a dry thickness of 1.5 microns (hydroquinone compound coated amount: 0.05 g/m$^2$).

A mixture of 9.9 g of Coupler (9) of the present invention, 0.8 g. of 2,5-di-tert-octylhydroquinone, 0.8 g of 6,6'-dihydroxy-7,7'-dimethyl-4,4,4',4'-tetramethylbis-2,2'-spirochroman, 10 ml of tricresyl phosphate and 30 ml of ethyl acetate was heated and dissolved on a steam bath and added to an aqueous solution containing 10 g of gelatin and 0.5 of sodium cetylsulfate, followed by vigorous mechanical stirring, thus obtaining a coupler dispersion. This coupler dispersion was mixed with 100 g of a photographic emulsion containing 4.7 × $10^{-2}$ mol of silver chlorobromide (silver chloride: 50 mol%, silver bromide: 50 mol%) and 9 g of gelatin, to which 3 ml of a 4% aqueous solution of 2-hydroxy-4,6-dichloro-s-triazine sodium salt, as a hardener, was then added, and the pH was adjusted to 6.3. The resulting mixture was coated in a dry thickness of 1.8 microns as a third layer (coupler coated amount: 4.2 × $10^{-4}$ mol/m$^2$; silver coated amount: 1.68 × $10^{-3}$ mol/m$^2$).

Then gelatin containing 2,5-di-tert-octylhydroquinone and, as an ultraviolet absorber, 2-(5-chlorobenzotriazol-2-yl)-4-methyl-6-tert-butylphenol and 2-(benzotriazol-2-yl)-4-tertbutylphenol was coated in a dry thickness of 2.5 microns as a fourth layer (hydroquinone compound coated amount: 0.05 g/m$^2$; benzotriazole compound coated amount: 0.4 g/m$^2$ of each), a redsensitive emulsion containing 2-[α-(2,4-di-tert-amylphenoxy)butyramido]-4,6-dichloro-5-methylphenol was coated in a dry thickness of 2.5 microns as a fifth layer (coupler coated amount: 0.98 × $10^{-3}$ mol/m$^2$; silver coated amount: 2.94 × $10^{-3}$ mol/m$^2$; silver bromide 50 mol%, silver chloride 50 mol%) and gelatin was then coated in a dry thickness of 1.0 micron as an uppermost layer, thus preparing a color print paper (Film C).

For comparison, another coupler dispersion was prepared in the same manner as described above but using 7.1 g. of a 4-position unsubstituted corresponding comparison coupler, i.e., 1-(2,4,6-trichlorophenyl)-3-(2-chloro-5-dodecylcarbamoylanilino)-3-oxo-2-pyrazoline (Comparison Coupler B), in place of Coupler (9) in the third layer of Film C, mixed with 200 g of an emulsion having the same composition and coated in a dry thickness of 2.8 microns as a third layer and thus another color print paper was prepared (Film D). In the third layer, 6.2 × $10^{-4}$ mol of the coupler and 4.96 × $10^{-3}$ mol of the silver halide were coated per m$^2$.

When these samples were subjected stepwise exposure and processing (stabilizing Bath (a)) similar to Example 2 and the reflection density was measured with green light, the photographic properties as shown in Table 4 were obtained. A clear color image of a main wavelength of 540 mµ was obtained.

Table 4

| Film | Coupler | Coating Amount Coupler (mol/m$^2$) | Coating Amount AgX (mol/m$^2$) | AgX/Coupler (molar ratio) | Fog | Gamma | Relative Sensitivity | Maximum Color Density |
|---|---|---|---|---|---|---|---|---|
| C | (9) | 4.2 × $10^{-4}$ | 1.68 × $10^{-3}$ | 4 | 0.05 | 2.43 | 100 | 2.40 |
| D | B | 6.2 × $10^{-4}$ | 4.96 × $10^{-3}$ | 8 | 0.05 | 2.52 | 98 | 2.45 |

It is apparent from the results in Table 4 that the light-sensitive material using the coupler of the present invention provides similar photographic properties to those of the prior art even though the coating amounts of the coupler and silver halide are reduced.

The light durability when the thus obtained developed films were exposed to a daylight type fluorescent lamp of 30,000 luxes through a filter capable of absorbing substantially all ultraviolet light having a wavelength of 400 mµ or less for 12 days, the heat durability when these films were allowed to stand at 80° C in the dark for one week and the humidity durability when these films were stored in the dark at 60° C and 75% RH (Relative Humidity) for two week are shown in Table 5 below by the ratio of the decrease in the density based on the initial density (in %).

Table 5

| | | Durability of Color Image (density decreasing ratio %) | | | | | | | | |
|---|---|---|---|---|---|---|---|---|---|---|
| | | Fluorescent Lamp 12 days Initial Density | | | 80° C, 1 week Initial Density | | | 60° C, 75% RH 2 weeks Initial Density | | |
| Film | Coupler | 0.5 | 1.0 | 2.0 | 0.5 | 1.0 | 2.0 | 0.5 | 1.0 | 2.0 |
| C | (9) | 14 | 9 | 5 | 7 | 5 | 3 | 8 | 5 | 3 |
| D | B | 18 | 13 | 8 | 19 | 12 | 7 | 16 | 10 | 6 |

EXAMPLE 4

Onto the opposite surface of a subbed cellulose acetate film support to which an antihalation layer containing carbon black had been coated were coated, as a first layer, a blue-sensitive silver iodobromide emulsion layer containing a yellow coupler, i.e., α-(2-methoxybenzoyl)-3-[α-(2,4-di-tertamylphenoxy)acetamido]acetanilide (coupler coated amount: 1.8 × $10^{-3}$ mol/m$^2$; silver coated amount: 1.2 × $10^{-2}$ mol/m$^2$), as a second layer, a gelatin intermediate layer, as a third layer, a red-sensitive silver chlorobromide emulsion layer containing a cyan coupler, i.e., 2-[α-(2,4-di-tert-amylphenoxy)butyramido]-4,6-dichloro-5-methylphenol (coupler coated amount: 1.4 × $10^{-3}$ mol/m$^2$; silver coated amount: 4.2 × $10^{-3}$ mol/m$^2$), as a fourth layer, a gelatin intermediate layer, and as a fifth layer, a coating solution which was prepared by mixing 100 g of a green-sensitive silver chlorobromide emulsion (silver chloride: 45 mol%; silver bromide 55 mol%; 6 × $10^{-2}$ mol of silver; 8.5 g of gelatin per 100 g of the emulsion) with the coupler dispersion having the composition set forth below.

Coupler (10) of the Present Invention; 6.8 g
Four-equivalent Corresponding Coupler C*; 7.0 g
2,5-Di-tert-octyl-hydroquinone; 0.5 g
Tricresyl Phosphate; 6 ml
Ethyl Acetate; 25 ml
Aqueous Solution of Gelatin (10 g) and Sodium Dodecylbenzene Sulfonate (0.5 g); 100 ml

* 1-(2,6-Dichloro-4-methoxyphenyl-3- 3-[α-(2,4-ditert-amylphenoxy)butyramido]benzamido -5-pyrazolone Coated Amount of Silver: 5.1 × 10⁻³ mol/m²
Coated Amount of Coupler: 9.8 × 10⁻⁴ mol/m²

Onto the layer, a gelatin protective layer was finally coated as a sixth layer to provide a color positive film.

The film was exposed stepwise through a red, green or blue filter and subjected to the following color processings to provide clear cyan, magenta and yellow color images having a good image quality without damaging the graininess with a smaller coated amount of silver than using the four-equivalent coupler alone.

| Color Processings | Temperature (° C) | Time |
|---|---|---|
| Pre-bath | 27 | 20 sec. |
| Water Washing | '' | 2 sec. |
| Color Development | 36 | 3 min. |
| Stopping | 27 | 40 sec. |
| Water Washing | '' | 40 sec. |
| First Fixing | '' | 40 sec. |
| Water Washing | '' | 40 sec. |
| Bleaching | '' | 1 min. |
| Water Washing | '' | 40 sec. |
| Second Fixing | '' | 40 sec. |
| Water Washing | '' | 1 min. |

The solutions employed in the above had the following compositions.

| Pre-bath Solution | |
|---|---|
| Sodium Borate (decahydrate) | 20 g |
| Sodium Sulfate (anhydrous) | 100 g |
| Sodium Hydroxide | 1 g |
| Water to make | 1 liter |
| Color Developer Solution | |
| Sodium Hexametaphosphate | 2 g |
| Sodium Sulfite | 4.35 g |
| 2-Methyl-4-(N,N-diethylamino)aniline Hydrochloride | 2.95 g |
| Sodium Carbonate (monohydrate) | 17.1 g |
| Sodium Bromide | 1.72 g |
| Water to make | 1 liter |
| Stopping Solution | |
| Glacial Acetic Acid | 15 ml |
| Water to make | 1 liter |
| Fixing Solution | |
| Sodium Thiosulfate | 153 g |
| Sodium Sulfite (anhydrous) | 15 g |
| Glacial Acetic Acid | 13.5 ml |
| Boric Acid | 7.5 g |
| Water to make | 1 liter |
| Bleaching Solution | |
| Potassium Ferricyanide (anhydrous) | 50 g |
| Potassium Bromide | 20 g |
| Water to make | 1 liter |

While the invention has been described in detail and with reference to specific embodiments thereof, it will be apparent to one skilled in the art that various changes and modifications can be made therein without departing from the spirit and scope thereof.

What is claimed is:

1. A photographic silver halide emulsion containing a two-equivalent magenta coupler, said coupler being capable of forming a magenta color image upon coupling reaction with an oxidation product of an aromatic primary amine developing agent, represented by the following general formula (I)

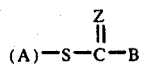         (I)

wherein (A) represents a residue of a 5-oxo-2-pyrazoline magenta color forming coupler or a residue of a pyrazolo-[1,5-a]-benzimidazole magenta color forming coupler;

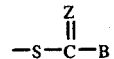

represents a group which is substituted for one hydrogen atom of the active methylene group in the coupler A; Z represents an oxygen atom or a sulfur atom; B represents a — Y group, a — D — Y group or a

group; D represents an oxygen atom or an — NR — group; R represents a hydrogen atom, an alkyl group or an aryl group; Y represents an alkyl group, an aryl group or a heterocyclic group; and Q in the

group represents the non-metallic atoms necessary to form a 5-membered or 6-membered nitrogen-containing heterocyclic ring, such atoms consisting of at least one carbon atom and of one or more nitrogen, oxygen or sulphur atoms.

2. The photographic silver halide emulsion as claimed in claim 1, wherein (A) represents a residue of a 5-oxo-2-pyrazoline magenta color forming coupler.

3. The photographic silver halide emulsion as claimed in claim 1 wherein (A) represents a residue of a pyrazole-[1,5-a]-benzimidazole magenta color forming coupler.

4. The photographic silver halide emulsion as claimed in claim 2, wherein said 5-oxo-2-pyrazoline coupler is represented by the following general formula (II), or (IV)

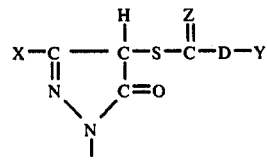  (II)

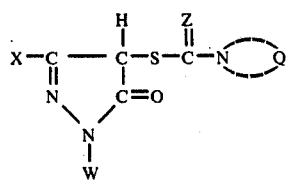  (IV)

wherein
W represents a hydrogen atom; or has up to 40 carbon atoms and represents a straight chain or branched chain alkyl group, an alkenyl group, a cycloalkyl group, an aralkyl group or a cycloalkenyl group, in which each of these groups can be substituted with a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyl group, an alkylsulfonyl group, an arylsulfonyloxy group, an alkylsulfonyloxy group, an arylthio group, an alkylthio group, an alkylsulfinyl group, an arylsulfinyl group, an alkylamino group, a dialkylamino group, an anilino group, an N-arylanilino group, an N-arylanilino group, an N-alkylanilino group, an N-acylanilino group, a hydroxy group or a mercapto group; an aryl group which can be substituted with one or more of a halogen atom, an alkyl group, an alkenyl group, a cycloalkyl group, an aralkyl group, a cycloalkenyl group, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group as substituents; a heterocyclic group which can be substituted with one or more of the substituents described above for the aryl group; an acyl group; a thioacyl group; an alkylsulfonyl group; an arylsulfonyl group; an alkylsulfinyl group; an arylsulfinyl group; a carbamoyl group; or a thiocarbamoyl group;

X represents a hydrogen atom; or has up to 40 carbon atoms and represents a straight chain or branched chain alkyl group; an alkenyl group, a cycloalkyl group, an aralkyl group, a cycloalkenyl group, in which each of these groups can be substituted with the respective substituents described above for W; an aryl group which can be substituted with one or more of the substituents for the aryl group as described above for W; a heterocyclic group which can be substituted with one or more of the substituents for the heterocyclic group as described above for W; an alkoxycarbonyl group; an aryloxycarbonyl group; an aralkyloxycarbonyl group; an alkoxy group; an aryloxy group; an alkylthio group; a carboxy group; an acylamino group; a diacylamino group; an N-alkylacylamino group; an N-arylacylamino group; a ureido group; a thioureido group; an alkoxycarbonylamino group, an aryloxycarbonylamino group, an alkoxythiocarbonylamino group, an aryloxythiocarbonylamino group, an anilino group; an alkylamino group; a heterocyclic amino group; a cycloamino group; an alkyl carbonyl group; an arylcarbonyl group; a sulfonamido group; a carbamoyl group; a sulfamoyl group; a guanidino group; a cyano group; an acyloxy group; a sulfonyloxy group; a hydroxy group; a mercapto group; a halogen atom or a sulfo group;

Y has up to 40 carbon atoms and represents a straight-chain or branched chain alkyl group, an alkenyl group, a cycloalkyl group; an aralkyl group, or a cycloalkenyl group, in which each of these groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, a sulfamoyl group, a carbamoyl group, an acylamino group, a diacylamino group, a ureido group, a thioureido group, a sulfonamido group, an alkoxycarbonylamino group, an aryloxycarbonylamino group, an alkoxythiocarbonylamino group, an aryloxythiocarbonylamino group, a heterocyclic group, an arylsulfonyl group, an alkylsulfonyl group, an arylsulfonyloxy group, an alkylsulfonyloxy group, an arylthio group, an alkylthio group, an alkylsulfinyl group, an arylsulfinyl group, an N-alkylamino group, or an N,N-dialkylamino group; an aryl group which can be substituted with one or more of an alkyl group, an aralkyl group, an alkenyl group, a cycloalkyl group, a cycloalkenyl group, a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, an N,N-dialkylsulfamoyl group, an N-alkyl-N-arylsulfamoyl group, N-alkylsulfamoyl group, N-arylsulfamoyl group, a carbamoyl group, an N-alkylcarbamoyl group, an N,N-dialkylcarbamoyl group, an N-alkyl-N-arylcarbamoyl group, an N-arylcarbamoyl group, an acylamino group, a diacylamino group, a ureido group, a thioureido group, a sulfonamido group, an alkoxycarbonylamino group, an aryloxycarbonylamino group, an alkoxythiocarbonylamino group, an aryloxythiocarbonylamino group, a heterocyclic group, an alkylsulfonyl group, an arylsulfonyl group, an alkylthio group, an arylthio group, an alkylsulfinyl group, an arylsulfinyl group, an N-alkylamino group, an N,N-dialkylamino group; a heterocyclic group which can be substituted with one or more of the substituents for the heterocyclic group as described above for the aryl group of Y;

Z represents an oxygen atom or a sulfur atom;

D represents an oxygen atom or an —NR— group;

R represents a hydrogen atom an alkyl group as defined above for Y, an aryl group as defined above for Y; and Q represents the non-metallic atoms necessary to form a 5-membered or 6-membered nitrogen-containing heterocyclic group, such atoms consisting of at least one carbon atom and of one or more nitrogen, oxygen or sulphur atoms; or is a symmetrical or asymmetrical complex coupler wherein the couplers of the above general formula (II) and (IV) are combined directly at W, X or Y or through a divalent moiety of the groups defined above for W, X or Y.

5. The photographic silver halide emulsion as claimed in claim 3, wherein said pyrazolo-[1,5-a]-benzimidazole coupler is represented by the following general formula (III) or (V)

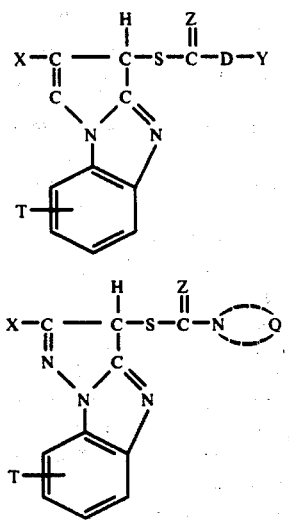

wherein

X represents a hydrogen atom or has up to 40 carbon atoms and represents a straight chain or branched chain alkyl group, an alkenyl group, a cycloalkyl group, an aralkyl group or a cycloalkenyl group, in which each of these groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyl group, an alkylsulfonyl group, an arylsulfonyloxy group, an alkylsulfonyloxy group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a heterocyclic amino group, a hydroxy group or a mercapto group; an aryl group which can be substituted with one or more of a halogen atom, an alkyl group, an alkenyl group, a cycloalkyl group, an aralkyl group, a cycloalkenyl group, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group; a heterocyclic group in which can be substituted with one or more of the substituents described above for the aryl group; an alkoxycarbonyl group; an aryloxycarbonyl group, an aralkyloxycarbonyl group; an alkoxy group; an aryloxy group; and alkylthio group; an arylthio group; a carboxy group; an acylamino group; a diacylamino group; an N-alkylacylamino group; an N-arylacylamino group; a ureido group; a thioureido group; an alkoxycarbonylamino group; an aryloxycarbonylamino group, an alkoxythiocarbonylamino group, an aryloxythiocarbonylamino group, an anilino group; an alkylamino group; a cycloamino group; an alkylcarbonyl group; an arylcarbonyl group; a sulfonamido group; a carbamoyl group; a sulfamoyl group; a guanidino group; a cyano group; and acyloxy group; a sulfonyloxy group; a hydroxy group; a mercapto group; a halogen atom or a sulfo group;

T represents a hydrogen atom or has up to 40 carbon atoms and represents a straight chain or branched chain alkyl group, an alkenyl group, a cycloalkyl group, an aralkyl group, or a cycloalkenyl group, in which each of these groups can be substituted with the respective substituents described above for X; an aryl group which can be substituted with one or more of the substituents for the aryl group as described above for X; a heterocyclic group, which can be substituted with one or more of the substituents for the heterocyclic group as described above for X; a cyano group; an alkoxy group; an aryloxy group; a halogen atom; a carboxy group; an alkoxycarbonyl group; an aryloxycarbonyl group; an acyloxy group; an alkylcarbonyl group, an acyloxy group; an alkylcarbonyl group; an arylcarbonyl group; an alkylthiocarbonyl group; an arylthiocarbonyl group; a diacylamino group; a ureido group; a thioureido group; an alkoxycarbonylamino group, an aryloxycarbonylamino group, an aryloxythiocarbonylamino group, a sulfonamido group; an alkylsulfonyloxy group; an arylsulfonyloxy group; an arylsulfonyl group; an alkylsulfonyl group; an arylthio group; an alkylthio group;an alkylsulfinyl group; an arylsulfinyl group; an alkylamino group; a dialkylamino group; an anilino group; an N-arylanilino group; an N-alkylanilino group; an N-acylanilino group; a hydroxy group and a mercapto group;

Y has up to 40 carbon atoms and represents a straight chain or branched chain alkyl group, an alkenyl group, a cycloalkyl group, an aralkyl group, a cycloalkenyl group in which, each of these groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, a sulfamoyl group, a carbamoyl group, an acylamino group, a diacylamino group, a ureido group, a thioureido group, a sulfonamido group, an alkoxycarbonylamino group, an aryloxycarbonylamino group, an alkoxythiocarbonylamino group, an aryloxythiocarbonylamino group, a heterocyclic group, an arylsulfonyl group, an alkylsulfonyl group, an arylsulfonyloxy group, an alkylsulfonyloxy group, an arylthio group, an alkylthio group, an alkylsulfinyl group; an arylsulfinyl group; an N-alkylamino group; or an N,N-dialkylamino group; an aryl group which can be substituted with one or more of an alkyl group, an aralkyl group, an alkenyl group, a cycloalkyl group, a cycloalkenyl group, a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, an N,N-dialkylsulfamoyl group, an N-alkyl-N-arylsulfamoyl group, an N-alkylsulfamoyl group, an N-arylsulfamoyl group, a carbamoyl group, an N-alkylcarbamoyl group, an N,N-dialkylcarbamoyl group, an N-alkyl-N-arylcarbamoyl group, an N-arylcarbamoyl group, an acylamino group, a diacylamino group, a ureido group, a thioureido group, a sulfonamido group, an alkoxycarbonylamino group, an aryloxycarbonylamino group, an alkoxythiocarbonylamino group, an aryloxythiocarbonylamino group, a heterocyclic group, an alkylsulfonyl group, an arylsulfonyl group, an alkylthio group, an arylthio group, an alkylsulfinyl group, an arylsulfinyl group, an N-alkylamino group, or an N,N-dialkylamino group; or a heterocyclic group which can be substituted with one or more of the substituents described above for the aryl group of Y;

Z represents an oxygen atom or a sulfur atom;

D represents an oxygen atom or an —NR— group;

R represents a hydrogen atom, an alkyl group as defined above for Y or an aryl group as defined above for Y; and Q represents the non-metallic atoms necessary to form a 5-membered or 6-membered nitrogen-containing heterocyclic group; such atoms consisting of at least one carbon atom and of one or more nitrogen, oxygen or sulphur atoms, or is a symmetrical or asymmetrical complex coupler wherein the couplers of the above general formula (III) and (V) are combined directly at T, X or Y or through a divalent moiety of the groups defined above for T, X or Y.

6. The photographic silver halide emulsion as claimed in claim 4, wherein W is a phenyl group in which at least one of the ortho positions is substituted with an alkyl group, an alkoxy group or a halogen atom.

7. The photographic silver halide emulsion as claimed in claim 2, wherein said 5-oxo-pyrazoline coupler is represented by formula (VI)

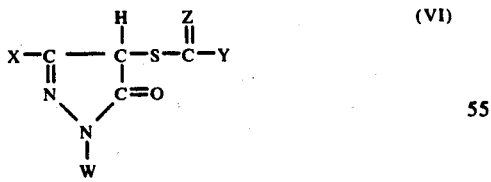

wherein

W represents a hydrogen atom; or has up to 40 carbon atoms and represents a straight chain or branched chain alkyl group, an alkenyl group, a cycloalkyl group, an aralkyl group or a cycloalkenyl group, in which each of these groups can be substituted with a halogen atom, a nitro group, a cyano group, and aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyl group, an alkylsulfonyl group, an arylsulfonyloxy group, an alkylsulfonyloxy group, an arylthio group, an alkylthio group, an alkylsulfinyl group, an arylsulfinyl group, an alkylamino group, a dialkylamino group, an anilino group, an N-arylanilino group, an N-arylanilino group, an N-alkylanilino group, an N-acylanilino group, a hydroxy group or a mercapto group; an aryl group which can be substituted with one or more of a halogen atom, an alkyl group, an alkenyl group, a cycloalkyl group, an aralkyl group, a cycloalkenyl group, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group as substituents; a heterocyclic group which can be substituted with one or more of the substituents described above for the aryl group; an acyl group; a thioacyl group; an alkylsulfonyl group; an arylsulfonyl group; an alkylsulfinyl group; an arylsulfinyl group; a carbamoyl group; or a thiocarbamoyl group;

X represents a hydrogen atom; or has up to 40 carbon atoms and represents a straight chain or branched chain alkyl group; an alkenyl group, a cycloalkyl group, an aralkyl group, a cycloalkenyl group, in which each of these groups can be substituted with the respective substituents described above for W; an aryl group which can be substituted with one or more of the substituents for the aryl group as described above for W; a heterocyclic group which can be substituted with one or more of the substituents for the heterocyclic group as described above for W; an alkoxycarbonyl group; an aryloxycarbonyl group; an aralkyloxycarbonyl group; an alkoxy group; an aryloxy group; an alkylthio group; an arylthio group; a carboxy group; an acylamino group; a diacylamino group; an N-alkylamino group; an N-arylacylamino group; a ureido group; a thioureido group; an alkoxycarbonylamino group, an aryloxycarbonylamino group, an alkoxythiocarbonylamino group, an aryloxythiocarbonylamino group, an anilino group; an alkylamino group; a heterocyclic amino group; a cycloamino group; an alkyl carbonyl group; an arylcarbonyl group; a sulfonamido group; a carbamoyl group; a sulfamoyl group; a guanidino group; a cyano group; an acyloxy group; a sulfonyloxy group; a hydroxy group; a mercapto group; a halogen atom or a sulfo group;

Y has up to 40 carbon atoms and represents a straight-chain or branched chain alkyl group, an alkenyl group, a cycloalkyl group; an aralkyl group, or a cycloalkenyl group, in which each of these groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, a sulfamoyl group, a carbamoyl group, an acylamino group, a diacylamino group, a ureido group, a thioureido group, a sulfonamido group, an alkoxycarbonylamino group, an aryloxycarbonylamino group, an alkoxythiocarbonylamino group, an aryloxythiocarbonylamino group, an aryloxythiocarbonylamino group, a heterocyclic group, an arylsulfonyl group, an alkylsulfonyl group, an arylsulfonyloxy group, an alkylsulfonyloxy group, an arylthio group, an alkylthio group, an alkylsulfinyl group, an arylsulfinyl group, an N-alkylamino group, or an N,N-dialkylamino group; an aryl group which can be substituted with one or more of an alkyl group, an aralkyl group, an alkenyl group, a cycloalkyl group, a cycloalkenyl group, a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, an N,N-dialkylsulfamoyl group, an N-alkyl-N-arylsulfamoyl group, N-alkylsulfamoyl group, N-arylsulfamoyl group, a carbamoyl group, an N-alkylcarbamoyl group, an N,N-dialkylcarbamoyl group, an N-alkyl-N-arylcarbamoyl group, an N-arylcarbamoyl group, an acylamino group, a diacylamino group, a ureido group, a thioureido group, a sulfonamido group, an alkoxycarbonylamino group, an aryloxycarbonylamino group, an alkoxythiocarbonylamino group, an aryloxythiocarbonylamino group, a heterocyclic group, an alkylsulfonyl group, an arylsulfonyl group, an alkylthio group, an arylthio group, an alkylsulfinyl group, an arylsulfinyl group, an N-alkylamino group, an N,N-dialkylamino group; a heterocyclic group which can be substituted with one or more of the substituents for the heterocyclic group as described above for the aryl group of Y;

Z represents an oxygen atom or a sulfur atom;

R represents a hydrogen atom an alkyl group as defined above for Y, an aryl group as defined above for Y; or is a symmetrical or asymmetrical complex coupler wherein the couplers of the above general formula (VI) are combined directly at W, X or Y or through a divalent moiety of the groups defined above for W, X or Y.

8. The photographic silver halide emulsion as claimed in claim 3 wherein said pyrazolo-[1,5-a]-benzimidazole coupler is represented by formula (VII)

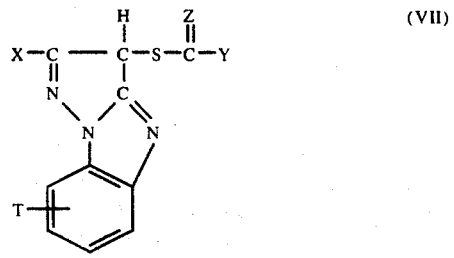

wherein

X represents a hydrogen atom or has up to 40 carbon atoms and represents a straight chain or branched chain alkyl group, an alkenyl group, a cycloalkyl group, an aralkyl group or a cycloalkenyl group, in which each of these groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyl group, an alkylsulfonyl group, an arylsulfonyloxy group, an alkylsulfonyloxy group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a heterocyclic amino group, a hydroxy group or a mercapto group; an aryl group which can be substituted with one or more of a halogen atom, an alkyl group, an alkenyl group, a cycloalkyl group, an aralkyl group, a cycloalkenyl group, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, an alkoxycarbonylamino group, an aryloxycarbonylamino group, an alkoxythiocarbonylamino group, an aryloxythiocarbonylamino group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group; a heterocyclic group in which can be substituted with one or more of the substituents described above for the aryl group; an alkoxycarbonyl group; an aryloxycarbonyl group, an aralkyloxycarbonyl group; an alkoxy group; an aryloxy group; an alkylthio group; an arylthio group; a carboxy group; an acylamino group; a diacylamino group; an N-alkylacylamino group; an N-arylacylamino group; a ureido group; a thioureido group; an alkoxycarbonylamino group, an aryloxycarbonylamino group, an alkoxythiocarbonylamino group, an aryloxythiocarbonylamino group, an anilino group; an alkylamino group; a cycloamino group; an alkylcarbonyl group; an arylcarbonyl group; a sulfonamido group; a carbamoyl group; a sulfamoyl group; a guanidino group; a cyano group; and acyloxy group; a sulfonyloxy group; a hydroxy group; a mercapto group; a halogen atom or a sulfo group;

T represents a hydrogen atom or has up to 40 carbon atoms and represents a straight chain or branched chain alkyl group, an alkenyl group, a cycloalkyl group, an aralkyl group, or a cycloalkenyl group, in which each of these groups can be substituted with the respective substituents described above for X; an aryl group which can be substituted with one or more of the substituents for the aryl group as described above for X; a heterocyclic group, which can be substituted with one or more of the substituents for the heterocyclic group as described above for X; a cyano group; an alkoxy group; an aryloxy group; a halogen atom; a carboxy group; an alkoxycarbonyl group; an aryloxycarbonyl group; an acyloxy group; an alkylcarbonyl group; an acyloxy group; an alkylcarbonyl group; an arylcarbonyl group; an alkylthiocarbonyl group; an arylthiocarbonyl group; a diacylamino group; a ureido group; a thioureido group; an alkoxycarbonylamino group, an aryloxycarbonylamino group, an aryloxythiocarbonylamino group, a sulfonamido group; an alkylsulfonyloxy group; an arylsulfonyloxy group; an arylsulfonyl group; an alkylsulfonyl group; an arylthio group; an alkylthio group; an alkylsulfinyl group; an arylsulfinyl group; an alkylamino group; a dialkylamino group; an anilino group; an N-arylanilino group; an N-alkylanilino group; an N-acylanilino group; a hydroxy group and a mercapto group;

Y has up to 40 carbon atoms and represents a straight chain or branched chain alkyl group, an alkenyl group, a cycloalkyl group, an aralkyl group, a cycloalkenyl group in which, each of these groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, a sulfamoyl group, a carbamoyl group, an acylamino group, a diacylamino group, a ureido group, a thioureido group, a sulfonamido group, an alkoxycarbonylamino group, an aryloxycarbonylamino group, an alkoxythiocarbonylamino groups, an aryloxythiocarbonylamino group, a heterocyclic group, an arylsulfonyl group, an alkylsulfonyl group, an arylsulfonyloxy group, an alkylsulfonyloxy group, an arylthio group, an alkylthio group, an alkylsulfinyl group, an arylsulfinyl group; an N-alkylamino group; or an N,N-dialkylamino group; an aryl group which can be substituted with one or more of an alkyl group, an aralkyl group, an alkenyl group, a cycloalkyl group, a cycloalkenyl group, a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, an N,N-dialkylsulfamoyl group, an N-alkyl-N-arylsulfamoyl group, an N-alkylsulfamoyl group, an N-arylsulfamoyl group, a carbamoyl group, an N-alkylcarbamoyl group, an N,N-dialkylcarbamoyl group, an N-alkyl-N-arylcarbamoyl group, an N-arylcarbamoyl group, an acylamino group, a diacylamino group, a ureido group, a thioureido group, a sulfonamido group, an alkoxycarbonylamino group, an aryloxycarbonylamino group, an alkoxythiocarbonylamino group, an aryloxythiocarbonylamino group, a heterocyclic group, an alkylsulfonyl group, an arylsulfonyl group, an alkylthio group, an arylthio group, an alkylsulfinyl group, an arylsulfinyl group, an N-alkylamino group, or an N,N-dialkylamino group; or a heterocyclic group which can be substituted with one or more of the substituents described above for the aryl group of Y;

Z represents an oxygen atom or a sulfur atom;

R represents a hydrogen atom, an alkyl group as defined above for Y or an aryl group as defined above for Y;

or is symmetrical or asymmetrical complex coupler wherein the couplers of the above general formula (VII) are combined directly at T, X or Y or through a divalent moiety of the groups defined above for T, X or Y.

9. The photographic silver halide emulsion as claimed in claim 7, wherein W is a phenyl group in which at least one of the ortho positions is substituted with an alkyl group, an alkoxy group or a halogen atom.

10. The photographic silver halide emulsion as claimed in claim 1, wherein Q is selected from the group consisting of pyrrolidine, piperidine, morpholine, imidazole, benzimidazole, phthalimide, succinimide glutarimide, hydantoin, oxazolidinedione, benzetriazole, α-pyridone, β-pyridone, oxazolidone, valerolactam, butyrolactam, thiohydantoin, naphthotriazole, tetrazole, pyrazole, indole, imidazoline, pyrazoline, piperazine, indoline and isoindoline.

11. A photographic color developer solution containing a primary aromatic amine developing agent and a two-equivalent magenta coupler, such coupler being capable of forming a magenta color image upon coupling reaction with an oxidation product of the aromatic primary amine developing agent, represented by the following general formula (I)

wherein (A) represents a residue of a 5-oxo-2-pyrazoline magenta color forming coupler or a residue of a pyrazolo-[1,5-a]-benzimidazole magenta color forming coupler;

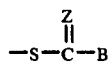

represents a group which is substituted for one hydrogen atom of the active methylene group in the coupler A; Z represents an oxygen atom or a sulfur atom; B represents a — Y group, a — D — Y group or a

group; D represents an oxygen atom or an — NR — group; R represents a hydrogen atom, an alkyl group or an aryl group; Y represents an alkyl group, an aryl group or a heterocyclic group; and Q in the

group represents the non-metallic atoms necessary to form a 5-membered or 6-membered nitrogen-containing heterocyclic ring, such atoms consisting of at least one carbon atom and of one or more nitrogen, oxygen or sulphur atoms.

12. A method of forming magenta color images which comprises developing an exposed silver halide photographic light-sensitive material with a developer containing a primary aromatic amine developing agent in the presence of a photographic magenta coupler, said coupler being capable of forming a magenta color image upon coupling reaction with an oxidation product of the aromatic primary amine developing agent, represented by the following general formula (I)

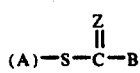     (I)

wherein (A) represents a residue of a 5-oxo-2-pyrazoline magenta color forming coupler or a residue of a pyrazolo-[1,5-a]-benzimidazole magenta color forming coupler;

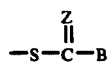

represents a group which is substituted for one hydrogen atom of the active methylene group in the coupler A; Z represents an oxygen atom or a sulfur atom; B represents a — Y group, a — D — Y group or a

group; D represents an oxygen atom or an — NR — group; R represents a hydrogen atom, an alkyl group or an aryl group; Y represents an alkyl group, an aryl group or a heterocyclic group; and Q in the

group represents the non-metallic atoms necessary to form a 5-membered or 6-membered nitrogen-containing heterocyclic ring, such atoms consisting of at least one carbon atom and of one or more nitrogen, oxygen or sulphur atoms.

13. A photographic light-sensitive material comprising a support having thereon a blue-sensitive silver halide emulsion layer, a green-sensitive silver halide emulsion layer containing the silver halide emulsion as claimed in claim 12, and a red-sensitive silver halide emulsion layer.

14. A photographic light-sensitive material comprising a support having thereon the photographic silver halide emulsion as claimed in claim 1.

* * * * *